(12) United States Patent
Kanazaki et al.

(10) Patent No.: US 8,491,908 B2
(45) Date of Patent: Jul. 23, 2013

(54) COMPOSITE PARTICLE, CONTRAST AGENT FOR PHOTOACOUSTIC IMAGING, AND METHOD FOR PRODUCING THE COMPOSITE PARTICLE

(75) Inventors: Kengo Kanazaki, Yokohama (JP); Tsutomu Honma, Fuchu (JP); Fumio Yamauchi, Yokohama (JP); Satoshi Ogawa, Tokyo (JP); Sachiko Inoue, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 20 days.

(21) Appl. No.: 13/115,276

(22) Filed: May 25, 2011

(65) Prior Publication Data
US 2011/0294987 A1 Dec. 1, 2011

(30) Foreign Application Priority Data
Jun. 1, 2010 (JP) ................. 2010-125659

(51) Int. Cl.
*A61K 39/44* (2006.01)
(52) U.S. Cl.
USPC ........................................ 424/179.1
(58) Field of Classification Search
None
See application file for complete search history.

(56) References Cited

U.S. PATENT DOCUMENTS

| | | | |
|---|---|---|---|
| 6,479,621 B2 | 11/2002 | Honma et al. |
| 6,586,562 B2 | 7/2003 | Honma et al. |
| 6,649,381 B1 | 11/2003 | Honma et al. |
| 6,686,439 B2 | 2/2004 | Kenmoku et al. |
| 6,803,444 B2 | 10/2004 | Suzuki et al. |
| 6,853,477 B2 | 2/2005 | Nomoto et al. |
| 6,861,496 B2 | 3/2005 | Kenmoku et al. |
| 6,861,550 B2 | 3/2005 | Honma et al. |
| 6,867,023 B2 | 3/2005 | Honma et al. |
| 6,908,720 B2 | 6/2005 | Kenmoku et al. |
| 6,916,861 B2 | 7/2005 | Nomoto et al. |
| 6,951,745 B2 | 10/2005 | Nomoto et al. |
| 7,153,622 B2 | 12/2006 | Honma et al. |
| 7,169,598 B2 | 1/2007 | Honma et al. |
| 7,267,974 B2 | 9/2007 | Kozaki et al. |
| 7,354,995 B2 | 4/2008 | Imamura et al. |
| 7,399,644 B2 | 7/2008 | Honma et al. |
| 7,615,233 B2 | 11/2009 | Yano et al. |
| 7,632,618 B2 | 12/2009 | Nomoto et al. |
| 8,093,060 B2 | 1/2012 | Hamachi et al. |
| 2008/0057561 A1 | 3/2008 | Takahashi et al. |
| 2008/0227664 A1 | 9/2008 | Honma et al. |
| 2011/0009601 A1* | 1/2011 | Yamauchi et al. ......... 530/387.3 |
| 2011/0294987 A1 | 12/2011 | Kanazaki et al. |

OTHER PUBLICATIONS

Andrew Tsourkas et al., "In Vivo Imaging of Activated Endothelium Using an Anti-VCAM-1 Magnetooptical Probe," 16 Bioconjugate Chem. 576-581 (2005).
Martin P. Mienkina et al., "Evaluation of Ferucarbotran (Resovist®) as a Photoacoustic Contrast Agent," 54 Biomed. Tech. 83-88 (2009).

* cited by examiner

*Primary Examiner* — Brian J Gangle
(74) *Attorney, Agent, or Firm* — Fitzpatrick, Cella, Harper & Scinto

(57) ABSTRACT

The present invention provides a composite particle having a high molar absorption coefficient for detection with higher detection sensitivity in photoacoustic imaging. In the present invention, a composite particle having a particle, a single-chain antibody which includes an antigen recognition region and a region other than the antigen recognition region and which is conjugated with the particle, and an organic dye conjugated with the single-chain antibody, in which the region other than the antigen recognition region of the single-chain antibody has thiol group, and a functional group of the particle is bound to the thiol group, is provided.

8 Claims, 7 Drawing Sheets

COMPOSITE PARTICLE, CONTRAST AGENT FOR PHOTOACOUSTIC IMAGING, AND METHOD FOR PRODUCING THE COMPOSITE PARTICLE

BACKGROUND OF THE INVENTION

1. Field of the Invention

The present invention relates to a composite particle, a contrast agent for photoacoustic imaging, and a method for producing the composite particle.

2. Description of the Related Art

Photoacoustic imaging (photoacoustic tomography) technique involves irradiating a certain localized surface portion of a sample to be measured with a pulsed light, measuring intensity of an acoustic signal generated by the irradiation light inside the sample to be measured, and processing the measurement results for imaging. The technique draws attention as a method to realize a cross-sectional image of a living body (sample) to be obtained by noninvasive measurement without possible exposure to radiation.

Contrast agents for photoacoustic imaging, that are used to improve detection sensitivity and contrast in photoacoustic imaging techniques, have been reported. A contrast agent administered into a living body is distributed in a living body tissue to be observed, absorbs a pulsed light energy irradiated to the tissue, and generates acoustic waves. Specifically, a contrast agent for photoacoustic imaging can increase an apparent molar absorption coefficient of a tissue containing the contrast agent for photoacoustic imaging. Thus, a contrast agent for photoacoustic imaging allows a tissue to be observed to be detected easily by adding acoustic waves generated by the contrast agent for photoacoustic imaging to acoustic waves generated in an endogenous tissue.

Here, as described in Biomed. Tech. 2009; 54: 83-88, RESOVIST (registered trade name), a contrast agent for MRI, contains a plurality of iron oxide particles coated with dextran, a polysaccharide, and is known to generate acoustic waves. However, since RESOVIST (registered trade name) contains iron oxide particles only for generation of acoustic waves, the acoustic wave generated by RESOVIST is relatively small. A contrast agent for photoacoustic imaging that generates a larger acoustic wave, that is, has a higher molar absorption coefficient, has been therefore awaited.

Bioconjugate Chemistry; 16(3), 576-581 discloses a composite particle including an iron oxide particle, wherein a dye and an antibody are bound to the surface of the particle. Since this composite particle includes an antibody, the composite particle binds to an antigen easily, enabling easy detection of an antigen site. It is believed that since this composite particle includes a dye, the molar absorption coefficient of the composite particle is higher than those of contrast agents containing iron oxide particles only, and therefore the composite particle can generate large acoustic waves.

SUMMARY OF THE INVENTION

In Bioconjugate Chemistry, 16(3), 576-581, a dye and an antibody are conjugated with a particle including an iron oxide particle. With this technique, however, the dye and the antibody compete with each other for binding due to limited numbers of functional groups on the particle surface, and conjugation of dye in large quantity is therefore difficult.

The composite particle according to a first embodiment of the present invention is a composite particle having a particle, a single-chain antibody which includes an antigen recognition region and a region other than the antigen recognition region and which is conjugated with the particle, and an organic dye conjugated with the single-chain antibody, in which the region other than the antigen recognition region of the single-chain antibody has thiol group, and a functional group of the particle is bound to the thiol group The composite particle according to a second embodiment of the present invention is a composite particle having a particle, a single-chain antibody which includes an antigen recognition region and a region other than the antigen recognition region and which is conjugated with the particle, and an organic dye conjugated with the single-chain antibody, wherein the single-chain antibody and the particle are conjugated via a thiol group in the region other than the antigen recognition region of the single-chain antibody.

The method for producing the composite particle according to a third embodiment of the present invention comprises binding a functional group of a particle to a thiol group in a region other than an antigen recognition region in a single-chain antibody that includes an antigen recognition region and the region other than the antigen recognition region and binding a functional group of an organic dye to at least any one of amino, carboxyl and hydroxyl groups of the single-chain antibody.

According to the present invention, since the particle is bound to the thiol group of the single-chain antibody while the functional group of the organic dye is bound to other functional group of the single-chain antibody, the competition of the single-chain antibody and the organic dye does not occur, and thereby a composite particle having both numbers of the single-chain antibody and the organic dye is provided.

Further, according to the present invention, since the region other than the antigen recognition region of the single-chain antibody has thiol group, and a functional group of the particle is bound to the thiol group, a reduction of binding ability of the single-chain antibody due to the conjugation with the particle is prevented.

Further features of the present invention will become apparent from the following description of exemplary embodiments with reference to the attached drawings.

DESCRIPTION OF THE EMBODIMENTS

Preferred embodiments of the present invention will now be described in detail in accordance with the accompanying drawings.

Composite particles according to embodiments of the present invention will be described below. However, the present invention is not limited to these embodiments.

Embodiment 1

The composite particle according to the present embodiment has a particle, a single-chain antibody having an antigen recognition region and a region other than the antigen recognition region and which is conjugated with the particle, and an organic dye conjugated with the single-chain antibody. The region other than the antigen recognition region of the single-chain antibody has thiol group, and a functional group of the particle is bound to the thiol group.

Further, in another composite particle according to the present embodiment, the single-chain antibody has at least any one of amino group, carboxyl group and hydroxyl group, and a functional group of the organic dye is bound to the at least any one of the amino group, carboxyl group and hydroxyl group. In this composite particle, since the particle is bound to the thiol group of the single-chain antibody while the functional group of the organic dye is bound to the at least any one of the amino group, carboxyl group and hydroxyl group of the single-chain antibody, a competition of number of the single-chain antibody and the organic dye binding to the particle does not occur, and thereby a composite particle having both numbers of the single-chain antibody and the organic dye is provided.

In the composite particles of the present embodiment, since the region other than the antigen recognition region of the single-chain antibody has thiol group, and a functional group of the particle is bound to the thiol group, a reduction of binding ability of the single-chain antibody due to the conjugation with the particle is prevented.

In the composite particle according to this embodiment, two or more single-chain antibodies can be preferably conjugated with the particle. When a large number of single-chain antibodies are present, the binding force of the composite particle according to this embodiment to an antigen appears to be increased.

Furthermore, two or more organic dyes can be conjugated with a single-chain antibody. When a large number of organic dyes are present, the molar absorption coefficient of the composite particle according to this embodiment appears to be increased.

Figure 1:
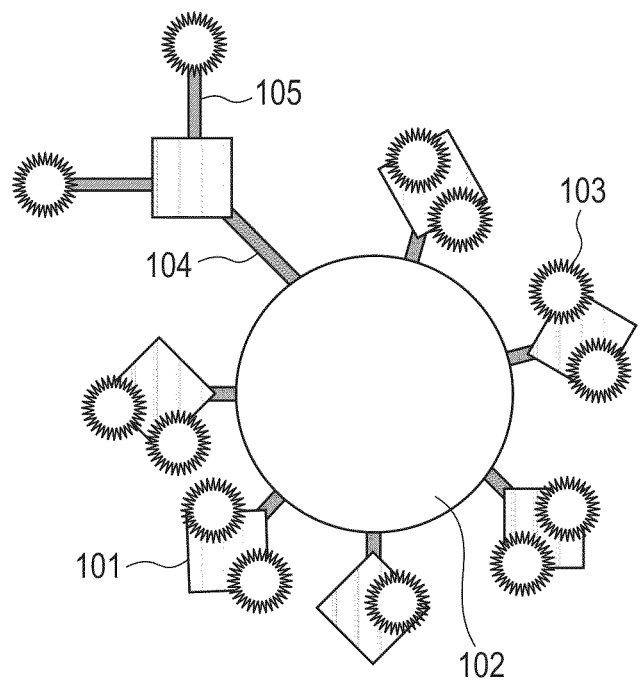
FIG. 1 is a schematic view of the composite particle according to the embodiment 1.

An example of the composite particle according to this embodiment will be described with reference to FIG. 1. FIG. 1 illustrates a part of a single-chain antibody 101, a particle 102, an organic dye 103, binding 104 between a thiol group in a region other than an antigen recognition region of the single-chain antibody and a functional group of the particle, and binding 105 between the at least any one of amino group, carboxyl group and hydroxyl group and a functional group that the organic dye has.

As noted above, in the composite particle according to the present embodiment, the region other than the antigen recognition region of the single-chain antibody has thiol group, and a functional group of the particle is bound to the thiol group. The binding between the thiol group and the functional group of the particle can be exemplified as thioester binding, thionoester binding, thioether binding, and thiol-maleimide coupling as represented in the formula below. Since thiol-maleimide coupling, i.e. binding between thiol group and meleimide group, can be reacted effectively and selectively in a pH range of neutral condition, the coupling is preferable.

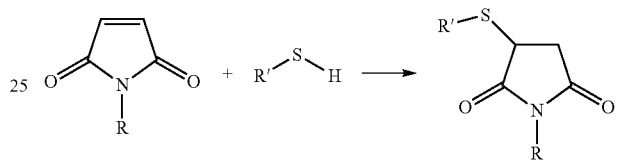

Further, in another composite particle according to the present embodiment, the single-chain antibody has at least any one of amino group, carboxyl group and hydroxyl group, and a functional group of the organic dye is bound to the at least any one of the amino group, carboxyl group and hydroxyl group. Among them, a binding between a nucleophilic amino group of the single-chain antibody and the functional group of the organic dye is particularly preferable. A number of nucleophilic amino groups are seen in a single-chain antibody, which can be found in the amino-terminal of the single-chain antibody or in a side chain of a lysine residue that constitutes the single-chain antibody. The organic dye may have any functional group as far as it can form the binding between the amino group, carboxyl group or hydroxyl group of the single-chain antibody. The functional group is exemplified as succinimidyl ester, succinimide, amino group or carboxyl group. The organic dye may originally have the functional groups, or the functional groups may be incorporated thereto by chemical reaction. The functional group of the organic dye and the single-chain antibody may be directly bonded, or bonded indirectly via a linker. Since an amide binding as shown below can be reacted effectively and selectively in a pH range of neutral condition, the binding is preferably exemplified as a binding between the amino group, carboxyl group or hydroxyl group of the single-chain antibody and the functional group of the organic dye.

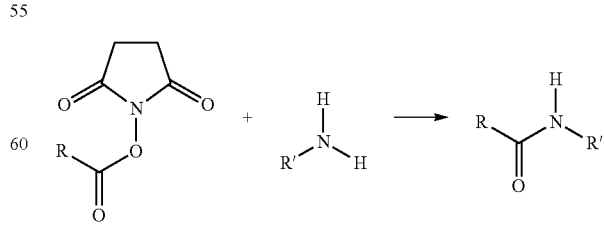

(Particle)

A particle used in the composite particle according to this embodiment is not particularly limited so long as the particle absorbs light and generates acoustic waves. As used herein, the term light includes ultraviolet light (electromagnetic waves having wavelengths of 10 nm to 400 nm), visible light (electromagnetic waves having wavelengths of 400 nm to 600 nm) and near-infrared light (electromagnetic waves having wavelengths of 600 to 1300 nm). The particle used in this embodiment can absorb near-infrared light and generate acoustic waves.

Examples of the particle according to this embodiment include a particle including an inorganic substance or an organic dye alone, a particle including an inorganic substance or an organic dye dispersed in another inorganic substance or in an organic substance, and a particle including an inorganic substance or an organic dye coated with another inorganic substance or with an organic substance. In this embodiment, any of these three types of particles or a combination thereof can be used.

Examples of the inorganic substance can include metal oxides, noble metal colloids, semiconductor particles, inorganic pigments and inorganic dyestuffs. In this embodiment, the particle can contain at least one of these inorganic substances and it may contain two or more inorganic substances. Examples of the metal oxides can include iron oxides ($Fe_2O_3$, $Fe_3O_4$), magnesium oxides, aluminium oxides, silicon dioxides, zinc oxides, titanium oxides, zirconium oxides, manganese oxides and boron oxides. Examples of the noble metal colloids can include colloids of gold, silver, copper and platinum. Examples of the semiconductor particles can include cadmium sulfides, zinc selenides, cadmium selenides, zinc tellurides, cadmium tellurides, zinc sulfides and lead sulfides. Examples of the inorganic pigments can include carbon black, fullerene and carbon nanotubes. Examples of the inorganic dyestuffs can include iron oxalates. Of these inorganic substances, an iron oxide particle is preferred.

In this embodiment, substances to be described in Section "Organic dyes" can be used as an organic dye forming a particle. Furthermore, in this embodiment, when a particle contains an organic dye having a hydrophilic segment, such as indocyanine green (ICG) to be described later, the particle preferably contains an additive such as a nicotinic acid derivative or a lipid having a positively-charged region. It appears that, since a lipid having a positively-charged region or a positively-charged region of a nicotinic acid derivative is associated with a hydrophilic region (a sulfonic acid group in case of ICG) in a dye, and the dye therefore becomes more hydrophobic, the dye can be solubilized in an organic solvent, such as chloroform or dichloromethane. A dye may be used as a desalted dye after treating the dye using a desalting column or the like.

The term "lipid having a positively-charged region" means a lipid that has a cationic substructure as a part of the structure thereof. Examples of such a lipid include glycerolipids such as phosphatidylcholine, phosphatidylethanolamine and phosphatidylserine; sphingolipids such as sphingomyelin, sphingophospholipid and sphingosine; glycolipids such as sphingoglycolipids having an amino sugar moiety such as neuraminic acid; synthetic cholesterols such as cholesteryl-3β-carboxyamidethylene-N-hydroxyethylamine and 3([N—(N',N'-dimethylaminoethane)-carbamoyl]cholesterol; synthetic lipids such as laurylamine, stearylamine, N-[1-(2,3-dioleyloxy)propyl]-N,N,N-trimethylammonium chloride (DOTMA) and 2,3-dioleyloxy-N-[2(sperminecarboxyamide)ethyl]-N,N-dimethyl-1-propanaminium trifluoroacetate (DOSPA); and ether-type phospholipids and cationic lipids. Examples of phosphatidylcholine, phosphatidylethanolamine and phosphatidylserine include diacylphosphatidylcholine, diacylphosphatidylethanolamine and diacylphosphatidylserine. In this embodiment, a preferred example of the lipid having a positively-charged region can be distearoylphosphatidylcholine.

Nicotinic acid derivatives used in this embodiment are not particularly limited. Examples thereof include nicotinic acid amide, benzyl nicotinate, nicotinic acid, methyl nicotinate, ethyl nicotinate, ethyl isonicotinate and tocopherol nicotinate.

In the composite particle according to this embodiment, a particle of any size can be used, but a nanoparticle of about 1 nm to 1000 nm is desirable. If the size exceeds 1000 nm, blood clots may be formed in the blood vessels. Sizes of 10 nm to 1000 nm can be particularly used. The size of the particle can be measured by known methods, such as transmission electron microscopy (TEM) observation or X-ray diffraction. Furthermore, the particle shape is not particularly limited, and different special structures, such as nanorod, nanocube, nanoprism and nanoshell, can be used. The size of the particle in the composite particle according to this embodiment can be three times or greater the size of an organic dye described later. Furthermore, the particle can be produced suitably by known particle production methods. Alternatively, commercially available particles can be used.

Examples of the organic substance for dispersion or coating of a particle can include polysaccharides, synthetic polymers, liposomes, polymer micelles, polyion complexes, fatty acids and surfactants. Examples of the inorganic substance for dispersion or coating of a particle can include silica, carbonates and hydroxyapatite. These organic and inorganic substances for dispersion or coating of the particle may be used solely or mixed with any of the organic and inorganic substances.

Examples of the polysaccharides can include dextran, pullulan, mannan, amylopectin, chitosan, xyloglucan, hyaluronic acid, algic acid, water-soluble cellulose, starch, agarose, carrageenan, heparin and derivatives thereof.

Examples of the synthetic polymers can include polymers having an amino group, such as polyethylenimine, polylysine, polyarginine, polyhistidine, polyallylamine and polyamide amine dendrimers; polymers having a hydroxyl group, such as polyvinyl alcohol and polyethylene glycol; polymers having a carboxyl group, such as polyglutamic acid, polyaspartic acid, polymalic acid, polymethacrylic acid and polyacrylic acid; and polylactic acid-glycolic acid copolymers.

Examples of phospholipids constituting the liposomes can include phosphatidylcholine, phosphatidylserine, phosphatidylinositol, phosphatidylglycerol, phosphatidylethanolamine, and sphingomyelin.

Examples of polymers forming the polymer micelles can include block copolymers containing a hydrophilic segment including polyethylene glycol and a hydrophobic segment selected from the group consisting of polylactide, poly(lactide-co-glycolide) and poly ε-caprolactone.

Examples of combinations of polymers forming the polyion complexes can include block copolymers containing a polycation segment selected from the group consisting of polyethylenimine, polylysine, polyarginine, polyhistidine and polyallylamine and block copolymers containing a polyanion segment selected from the group consisting of polyglutamic acid, polyaspartic acid, polymalic acid, polymethacrylic acid and polyacrylic acid.

Examples of fatty acids can include saturated fatty acids such as lauric acid, myristic acid, palmitic acid and stearic acid; unsaturated fatty acids such as lauroleic acid, physeteric acid, myristoleic acid, palmitoleic acid, petroselinic acid and oleic acid; and branched fatty acids such as isolauric acid, isomyristic acid, isopalmitic acid and isostearic acid.

Examples of the surfactants include polyoxyethylene alkyl ether, alkyl sulfides, polyoxyethylene sorbitan monolaurate, N-(carbonyl-methoxypolyethyleneglycol 2000)-1,2-distearoyl-sn-glycero-3-phosphoethanolamine sodium salt which is a polyethylene-glycolated phospholipid having a methoxy group at an end, and N-(aminopropylpolyethyleneglycol 2000)carbamyl-distearoylphosphatidyl-ethanolamine which is a polyethylene-glycolated phospholipid having a primary amino group at an end. Furthermore, a functional group at an end may be easily bound with a single-chain antibody to be described later by binding another substance to a surfactant. For example, a maleimide group can be introduced into an end by binding a succinimidyl-[(N-maleimidopropionamido)-diethyleneglycol]ester to the above-mentioned primary amino group of N-(aminopropylpolyethyleneglycol 2000)carbamyl-distearoylphosphatidyl-ethanolamine.

The particle according to the present embodiment has a functional group which can bind to the thiol group in the region other than the antigen recognition region. The functional group may be carboxyl group, maleimide group, alkyl halide group, amino group or hydroxyl group. The particle may originally have the functional groups, or the functional groups may be incorporated thereto by chemical reaction.

In this embodiment, the region other than the antigen recognition region of the single-chain antibody can have a cysteine (C), and a thiol group of the C may form the before mentioned thiol-maleimide coupling with a maleimide group of the particle.

(Single-Chain Antibody)

The single-chain antibody of the composite particle of the present embodiment includes an antigen recognition region and a region other than the antigen recognition region, and the region other than the antigen recognition region has a thiol group.

As used herein, the term "single-chain antibody" means a polypeptide in which a heavy chain variable region (VH domain) and a light chain variable region (VL domain) of an antibody are linked with a peptide linker. The peptide linker includes 15 amino acids, for example. The antigen recognition region of an single-chain antibody is a heavy chain variable region and a light chain variable region, which has a sequence including complementary determining regions (hereinafter, referred to as CDR) and framework regions. The CDRs exist in the vicinity of the binding interface with the target molecule and is closely involved in the specific binding with the target molecule. Meanwhile, the framework regions are indirectly involved in the binding by forming a CDR structure that can bind to the target molecule. Thus, the CDRs and the frameworks act on each other and express the function of the single-chain antibody. The region other than the antigen recognition region is a region other than these regions. In this embodiment, the single-chain antibody can be a humanized single-chain antibody.

Single-chain antibodies can be produced for various antigens inexpensively and conveniently. In addition, since single-chain antibodies have lower molecular weights than conventional antibodies, the amount of antibody bound to each particle can be increased. Furthermore, since single-chain antibodies do not have the Fc region (constant region) of the antibody, antigenicity can be reduced.

The term "antibody" is a generic name of immunoglobulin family proteins that are induced in response to a specific antigen or substance through the immune system. An antibody recognizes a specific target molecule and can bind to this target molecule. The strength of binding to this target molecule can be a dissociation binding constant KD (the lower the value is, the higher the binding affinity is) with the target molecule of 1 µM or less. The antibody can be a mouse antibody, a human antibody, a humanized antibody, or a chimera antibody or can be derived from other species. Moreover, the antibody can be selected from the group consisting of monoclonal and polyclonal antibodies. Furthermore, an antibody fragment, a portion of the antibody, which is a lower-molecular-weight derivative of the antibody capable of binding to a target molecule may be used. Examples of the antibody fragment include a Fab fragment (hereinafter, also abbreviated to "Fab"), a Fab' fragment (hereinafter, also abbreviated to "Fab'"), F(ab'), F(ab')$_2$, a heavy chain variable (VH) domain alone, a light chain variable (VL) domain alone, a VH-VL complex, a camelized VH domain, and a peptide containing an antibody complementarity determining region (CDR).

Preferred examples of the single-chain antibody can include a polypeptide represented by the amino acid sequence of SEQ ID NO: 1.

(SEQ ID NO: 1)
MDIQMTQSPSSLSASVGDRVTITCRASQDVNTAVAWYQQK

PGKAPKLLIYSASFLYSGVPSRFSGSRSGTDFTLTISSLQPEDFATYYCQ

QHYTTPPTFGQGTKVEIKGGGGSGGGGSGGGGSEVQLVESGGGLVQPGGS

LRLSCAASGFNIKDTYIHWVRQAPGKGLEWVARTYPTNGYTRYADSVKGR

FTISADTSKNTAYLQMNSLRAEDTAVYYCSRWGGDGFYAMDYWGQGTLVT

VSSAAALEHHHHHHGGC

The amino acid sequence, excluding an amino acid M (the 1st residue) at the amino terminus and the 244th residue to the 257th residue and the 109th residue to the 123rd residue on the carboxyl terminus side, is a structural unit that can express a function of binding specifically to an antigen, i.e., an antigen recognition region. In other words, in SEQ ID NO: 1, M (the 1st residue), the 244th residue to the 257th residue and GGGGSGGGGSGGGGS (from the 109th residue to the 123rd residue) are a region other than the antigen recognition region. from the 109th residue to the 123rd residue is a peptide linker that links the VH domain and the VL domain.

In a case of the above mentioned single-chain antibody, the thiol group existing in the side chain of the 257th cysteine (C) among the amino acid sequence of the 244th residue to the 257th residue can be the thiol group of the region other than the antigen recognition region. Since the thiol group is bound to a functional group of the particle, a reduction of binding ability of the single-chain antibody due to the conjugation with the particle is prevented. Further, since the binding between the single-chain antibody and the particle affects little to the antigen recognition region, the structure of the single-chain antibody is less likely to be unstable, and thus aggregation of the single-chain antibody is less likely to be occurred. Consequently, dispersibility of the composite particles is maintained.

The above amino acid sequence of the single-chain antibody includes amino acid residues having amino group, carboxyl group or hydroxyl group, which groups enables the binding to the below mentioned organic dye. The sequence of the single-chain antibody includes amino group of the amino terminal, or amino acid residues having nucleophilic amino group in the side chain such as lysine (K) (the 40th, 43rd, 46th, 104th, 108th, 152nd, 166th, 188th and 199th residue), which enable amido binding, for example, between succinimidyl ester reactive dye and the single-chain antibody having the nucleophilic amino group.

It is more preferable when the amino group in the side chain of lysine residues in the sequence of the single-chain antibody and the carboxyl group of the organic dye represented in below mentioned formula (1)

(Target Molecule)

A composite particle in this embodiment can be particularly used for photoacoustic imaging for the diagnosis of an affected tissue, such as a tumor. It is desirable that the composite particle according to this embodiment recognize a target molecule or bind to a target molecule. The "target molecule" is not particularly limited so long as the sample molecule is derived from an organism, and can mean a sample molecule that is located specifically at a lesion site, particularly a sample molecule expressed at a specific tumor site. Examples of the target molecule include tumor antigens, receptors, membrane proteins on the cell surface, proteolytic enzymes and cytokines. The target molecule in the present invention can be a tumor antigen.

Specific examples of the tumor antigen include the vascular endothelial growth factor (VEGF) family, the vascular endothelial growth factor receptor (VEGFR) family, the prostate specific antigen (PSA), the carcinoembryonic antigen (CEA), the matrix metalloproteinase (MMP) family, the epidermal growth factor receptor (EGFR) family, the epidermal growth factor (EGF), integrin family, type 1 insulin-like growth factor receptors (IGF-1Rs), CD184 antigen (CXC chemokine receptor 4 [CXCR4]) and placental growth factor (PlGF). Human epidermal growth factor receptor 2 (hereinafter, may be referred to as HER2) in the EGFR family can be particularly included. The term HER2 as used herein may be referred to as ErbB2, c-Erb-B2 or p185HER2. HER2 is a member of the EGFR family and is one of tyrosine kinase receptors. HER2 is a substance (protein) whose gene is amplified and overexpressed in adenocarcinomas, such as breast cancer, prostatic cancer, gastric cancer, ovary cancer and lung cancer. HER2 is activated by forming a dimer (may be referred to as a homodimer) of HER2 or forming a dimer (may be referred to as a heterodimer) with another EGFR. More specifically, it is believed that HER2 is self-phosphorylated by forming a homodimer or a heterodimer, and then a cell growth signal is transduced into the nucleus, resulting in cell growth, infiltration, metastasis and apoptosis suppression. An antibody that binds specifically to the tumor antigen is easily obtained for those skilled in the art. For example, such an antibody for the use can be prepared suitably by known antibody production methods using the antigen or a partial peptide thereof as an immunogen. A single-chain antibody can also be obtained as a recombinant protein by gene recombination based on gene sequence information of the prepared antibody. A commercially available antibody may also be used.

(Organic Dye)

An organic dye of the composite particle according to this embodiment is not particularly limited so long as the organic dye absorbs a light and generates acoustic waves. The term light used herein means ultraviolet light (electromagnetic waves having wavelengths of 10 nm to 400 nm), visible light (electromagnetic waves having wavelengths of 400 nm to 600 nm), near-infrared light (electromagnetic waves having a wavelengths of 600 to 1300 nm), or the like. An organic dye in this embodiment can be one that absorbs a near-infrared light and generates acoustic waves.

Absorption characteristics of the composite particle according to this embodiment suitable for the wavelengths of irradiation light can be set by using an organic dye that absorbs light in the near-infrared light range.

Examples of organic dyes used in the composite particle according to this embodiment can include azine dyes, acridine dyes, triphenylmethane dyes, xanthene dyes, porphyrin dyes, cyanine dyes, phthalocyanine dyes, styryl dyes, pyrylium dyes, azo dyes, quinone dyes, tetracycline dyes, flavone dyes, polyene dyes and BODIPY (Invitrogen, registered trade name) dyes. An organic dye may be used solely or mixed with any other organic dyes.

Examples of the porphyrin dyes can include a prescription drug PHOTOFRIN (Wyeth K.K.), LASERPHYRIN (Meiji Seika Kaisha, Ltd.) and VISUDYNE (Novartis Pharma AG).

Examples of the cyanine dye can include indocyanine green (hereinafter, referred to as ICG), ALEXA FLUOR (Invitrogen, registered trade name), CY (GE HEALTHCARE Biosciences, registered trade name) and DYLIGHT (Pierce Biotechnology, Inc.) dyes. Furthermore, preferred examples include a compound represented by the following formula (1) and a compound represented by the following formula (2).

Formula 1

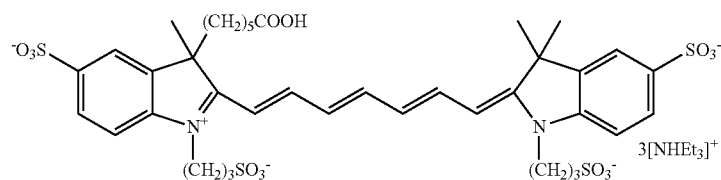

(1)

Formula 2

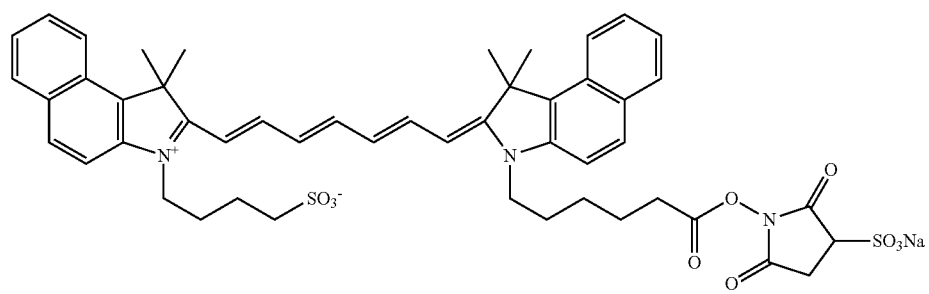

(2)

The structure of ICG is represented by the following formula (3).

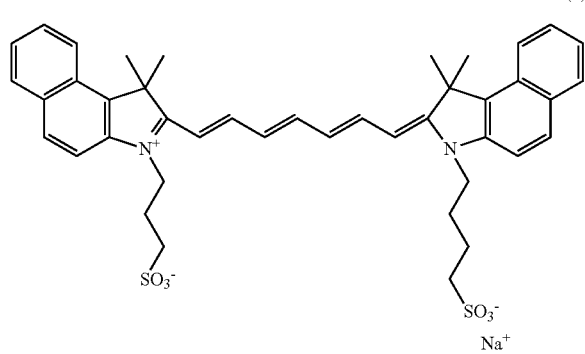

Examples of the phthalocyanine dyes can include IRDYE (LI-COR, registered trade name).

The size of the above-described organic dye can be 3 nm or shorter, and further can be 2 nm or shorter.

In the composite particle of the present embodiment, the organic dye has a functional group which can bind to the single-chain antibody. The organic dye may have any functional group as far as it can form the binding between the amino group, carboxyl group or hydroxyl group of the single-chain antibody. The functional group is exemplified as succinimidyl ester, succinimide, amino group or carboxyl group. The organic dye may originally have the functional groups, or the functional groups may be incorporated thereto by chemical reaction. The functional group of the organic dye and the single-chain antibody may be directly bonded, or bonded indirectly via a linker.

Embodiment 2

The composite particle according to this embodiment is a composite particle including a single-chain antibody, a particle and an organic dye, wherein the single-chain antibody and the particle are conjugated via a thiol group in a region other than an antigen recognition region of the single-chain antibody.

In the composite particle according to this embodiment, the single-chain antibody and the organic dye can be conjugated via an amino group of the single-chain antibody.

The single-chain antibody, the particle and the organic dye of the composite particle according to this embodiment are as described above.

Embodiment 3

In this embodiment, a contrast agent for photoacoustic imaging will be described.

(Contrast Agent for Photoacoustic Imaging)

The contrast agent for photoacoustic imaging according to this embodiment has the above-described composite particle and a dispersion medium.

(Dispersion Medium)

The above-mentioned dispersion medium is a liquid substance for dispersing the composite particle according to this embodiment. Examples of the dispersion medium include phosphate buffered saline (PBS), physiological saline and distilled water for injection. In the contrast agent according to this embodiment, the above-described composite particle according to this embodiment may be dispersed in this dispersion medium beforehand. Alternatively, the composite particle according to this embodiment and a dispersion medium are included in a kit, and the composite particle may be dispersed in the dispersion medium before administration into a living body and may be used.

Embodiment 4

In this embodiment, a method for producing a composite particle will be described.

(Method for Producing a Composite Particle)

The method for producing a composite particle according to this embodiment includes: binding a thiol group in a region other than an antigen recognition region of a single-chain antibody including an antigen recognition region and the region other than the antigen recognition region, and a functional group of a particle; and binding at least any one of an amino group, a carboxyl group and a hydroxyl group of the single-chain antibody and a functional group of an organic dye.

In this embodiment, a particle and a single-chain antibody are conjugated via a thiol group in a region other than an antigen recognition region of the single-chain antibody. Examples of the bond of the particle and the thiol group can include a thio-ester bond, thiono-ester bond, thio-ether bond and thiol-maleimide coupling. Thiol-maleimide coupling, i.e., a bond of a thiol group and a maleimide group can be particularly used because a reaction can be performed efficiently and selectively in a neutral pH range. A particle conjugated with a single-chain antibody by the reaction can be washed and purified by ultrafiltration or size exclusion column chromatography.

In this embodiment, a single-chain antibody conjugated with a particle and an organic dye are conjugated by a conventionally known coupling reaction via an amino group, a carboxyl group or a hydroxyl group, particularly via an amino group. The amino group exists in the amino terminus of a single-chain antibody and a side chain of a lysine residue, an amino acid constituting the single-chain antibody. Many amino groups are contained in the single-chain antibody. Furthermore, a reaction can be performed efficiently and selectively in a neutral pH range. An organic dye conjugated with the single-chain antibody by the reaction can be washed and purified by ultrafiltration or size exclusion column chromatography.

Embodiment 5

In this embodiment, photoacoustic imaging will be described (photoacoustic imaging).

The composite particle according to this embodiment can be used for photoacoustic imaging. Photoacoustic imaging using the composite particle according to this embodiment has at least administering the composite particle according to this embodiment to a sample or a specimen obtained from the sample, irradiating the sample or the specimen obtained from the sample with pulsed light, and measuring a photoacoustic signal derived from the composite particle existing in the sample or in the specimen obtained from the sample.

One example of photoacoustic imaging using the composite particle according to this embodiment is described below. Specifically, the composite particle according to this embodiment is administered to a sample or added to a specimen such as an organ obtained from the sample. It should be noted that the sample is not particularly limited and refers to a mammal, such as humans, laboratory animals and pets, and any other organisms. Examples of the specimen in a sample or obtained from a sample can include organs, tissues, tissue sections, cells and cell lysates. After administration or addition of the composite particle, the sample or the like is irradiated with a laser pulsed light in the near-infrared wavelength range.

In the photoacoustic imaging according to this embodiment, the wavelengths of irradiation light can be selected depending on the laser light source used. In the photoacoustic imaging according to this embodiment, a sample can be irradiated with light having wavelengths of 600 nm to 1300 nm in the near-infrared light range, which is minimally affected by absorption or diffusion of light in a living body and called "the biological window," to obtain an acoustic signal efficiently.

A photoacoustic signal (acoustic wave) from the composite particle according to this embodiment is detected and converted to an electric signal with an acoustic wave detector, e.g., a piezoelectric transducer. Based on this electric signal obtained by an acoustic wave detector, distribution of optical characteristic values, such as the position in and the size of an absorber in the sample or the like and molar absorption coefficient, can be calculated. For example, if the composite particle is detected with values equal to or higher than standard thresholds, the target molecule or a site of production of the target molecule is considered to exist in the sample, or it can be presumed that the target molecule exists in the specimen, or a site of production of the target molecule exists in the sample from which the specimen is derived.

Since the composite particle according to this embodiment has a single-chain antibody, the composite particle can be used in photoacoustic imaging of the target molecule expressed specifically in a tumor. For example, the composite particle according to this embodiment can be used for the diagnosis of a tumor that correlates with the amount of an antigen. The composite particle can also be used in photoacoustic imaging of a tumor antigen associated with breast cancer. Using cultured cells or tissues as a measurement specimen, the composite particle according to this embodiment can also be used for the purpose of research of a disease. Meanwhile, the composite particle according to this embodiment can also be used for photoacoustic imaging even when the composite particle does not have a specific bond to a target molecule.

Furthermore, the composite particle according to this embodiment can be used in photoacoustic imaging of the target molecule for the purpose of diagnosis of a disease in a patient or diagnosis for prevention of a disease in a healthy individual by introducing the composite particle into a sample or a cell or a tissue obtained from the sample. The diagnosis method by photoacoustic imaging using the composite particle according to this embodiment has introducing the composite particle according to this embodiment into a cultured cell, a cell or a tissue collected from a sample, or the sample and monitoring the position and condition of a disease by detecting a signal from the composite particle.

EXAMPLES

Hereafter, the present invention will be described with reference to the Examples. However, the scope of the present invention is not limited to these Examples.

(Evaluation of Photoacoustic Characteristics)

Measurement of photoacoustic signal intensity described in the Examples below was performed with the following apparatuses and conditions.

The conditions of the measurement using Model Titanium Sapphire Laser (Lotis Tii) as a light source were a wavelength of 750 nm, an energy density of 21.8 mJ/cm$^2$, a pulse width of 20 nanoseconds, and a pulse frequency of 10 Hz.

The conditions of the measurement using Model V303 (Panametrics-NDT) as an ultrasonic wave transducer were a central frequency band of 1 MHz, an element size of φ0.5, a measurement distance of 33 mm (Non-focus), and amplification of +20 dB (ultrasonic preamplifier Model 5682, Olympus Corporation).

A polystyrene cuvette having an optical path length of 0.1 cm was used as a measurement vessel. Using DPO3034 (Tektronix) as a gauge and the light detection of photoacoustic light with a photodiode as a trigger, data was acquired and calculated as the mean value of measurement 32 times (32 pulses).

Example 1

(Synthesis of Single-Chain Antibody)

First, a gene fragment of a single-chain antibody was prepared based on the gene sequence of the variable region of an immunoglobulin G (IgG) bound to HER2. His6 tag having six consecutive histidine residues and a gene sequence encoding a cysteine residue were positioned at the 3' terminus of the prepared gene for purification. To obtain a bacterial strain for expression, *Escherichia coli* (BL21 strain) was transformed with plasmid pET-22b(+) (Merck [Novagen]) into which this gene fragment was inserted. The obtained bacterial strain was cultured overnight in 4 mL of LB-Amp medium, the whole volume was added to 250 mL of 2×YT-Amp medium, and the mixture was cultured with shaking at 120 rpm at 28° C. for 8 hours. Then, isopropyl-β-thiogalactopyranoside (IPTG) was added to obtain a final concentration of 1 mM, and the culture was continued at 28° C. for approx. 20 hours. The culture broth was centrifuged at 4° C. and 8000×g for 30 minutes to collect IPTG-induced *Escherichia coli*, and a supernatant culture broth was collected Ammonium sulfate was added to the obtained culture broth to obtain 80% saturation, and proteins were precipitated by salting out. The solution subjected to salting out was allowed to stand at 4° C. for 12 hours and centrifuged at 4° C. and 8000×g for 30 minutes to recover a precipitate. The obtained precipitate was dissolved in 20 mL of 20 mM Tris HCl/500 mM NaCl buffer and dialyzed with 1 L of this buffer three times. The dialyzed protein solution was added to a column filled with HIS•BIND (Merck [Novagen], registered trade name) Resin and purified by metal chelate affinity chromatography using Ni ion.

The amino acid sequence of the single-chain antibody prepared as described above was as follows:

(SEQ ID NO: 1)
MDIQMTQSPSSLSASVGDRVTITCRASQDVNTAVAWYQQK

PGKAPKLLIYSASFLYSGVPSRFSGSRSGTDFTLTISSLQPEDFATYYCQ

QHYTTPPTFGQGTKVEIKGGGGSGGGGSGGGGSEVQLVESGGGLVQPGGS

LRLSCAASGFNIKDTYIHWVRQAPGKGLEWVARTYPTNGYTRYADSVKGR

FTISADTSKNTAYLQMNSLRAEDTAVYYCSRWGGDGFYAMDYWGQGTLVT

VSSAAALEHHHHHHGGC

The amino acid sequence, excluding an amino acid M (the 1st residue) at the amino terminus, from the 244th residue to the 257th residue at the carboxyl terminus, and from the 109th residue to the 123rd residue is a structural unit that can express a function of binding specifically to an antigen, i.e., the antigen recognition region. Therefore, a thiol group in a region other than the antigen recognition region of the single-chain antibody prepared in this Example is the thiol group that exists in the side chain of cysteine (C), the 257 residue of the amino acid sequence of from the 244th residue to the 257 residue.

The buffer was replaced with a phosphate buffer (Kishida Chemical Co., Ltd.) containing 5 mM EDTA (Kishida Chemical Co., Ltd.), tri(2-carboxyethyl)phosphine hydrochloride (TCEP, PIERCE) was added to the purified single-chain antibody in an amount of 20 times the amount of the antibody, and the mixture was subjected to reduction treatment at 25° C. for approximately 2 hours. The phosphate buffer used herein is a solution of pH 7.4 that contains 2.68 mM KCl, 137 mM NaCl, 1.47 mM $KH_2PO_4$, 1 mM $Na_2HPO_4$ and 5 mM EDTA.

(Conjugation of an Iron Oxide Particle Having a Maleimide Group and a Single-Chain Antibody)

A method for conjugating an iron oxide particle via a thiol group of this region other than an antigen recognition region will be described below.

An iron oxide particle-containing dextran particle (particle size, 20 nm) produced by micromod Partikel-Technolgie that had a maleimide group (hereinafter, referred to as "IO20") was used as a particle. IO20 and the reduced single-chain antibody in amount of 100 times the amount of IO20 were mixed with Iron Oxide Particle (1), the mixture was slowly stirred at 25° C. for 4 hours, and then an L-cysteine solution (Kishida Chemical Co., Ltd.) was added to obtain a final concentration of 1 mM. Subsequently, the mixture was purified by size exclusion column chromatography using a column equilibrated with a phosphate buffer (pH=7.4), and then the buffer was replaced with 0.05 M carbonic acid buffer (pH=9.6).

The quantity of unreacted single-chain antibody eluted from the size exclusion column was determined, and the quantity of single-chain antibody conjugated with each IO20 was approx. 11.

Here, since a maleimide group is strongly bound to a thiol group, the single-chain antibody and the IO20 appears to be conjugated via a thiol-maleimide coupling. In other words, it appears that a complex (hereinafter, referred to as "single-chain antibody-IO20 complex") comprising IO20 conjugated with a single-chain antibody was obtained. Hereinafter, a bounded body is referred to as a complex, and a bounded body of the complex and an organic dye is referred to as a composite particle.

(Conjugation of Single-Chain Antibody-IO20 Complex and Organic Dye)

A solution of a saccinimidyl ester reactive dye (Invitrogen), a compound represented by the above-mentioned formula (1), in dimethyl sulfoxide was added to the single-chain antibody-IO20 complex in amount of 20, 100, 500, or 1000 times the amount of the complex, and the mixture was slowly stirred at 25° C. for 2 hours. After stirring, the mixture was purified using a PD-10 desalting column (GE HEALTHCARE Biosciences) equilibrated with a phosphate buffer (pH=7.4) to obtain 4 types of composite particles (hereinafter, referred to as dye-conjugated IO20 particles) conjugated with a saccinimidyl ester reactive dye, which is an organic dye. Here, a lysine (K) residue exists in the sequence of the single-chain antibody prepared in this Example. Since this lysine residue has a primary amino group which is a nucleophilic group in a side chain of the single-chain antibody, it appears that a bond of an amino group and a carboxyl group (amide bond) was formed by mixing the succinimidyl ester reactive dye used in the Example, and thereby the organic dye and the single-chain antibody were conjugated.

(Measurement of Molar Absorption Coefficient of Composite Particles)

The number of organic dyes that were conjugated with the prepared dye-conjugated IO20 particle and the molar absorption coefficient at 750 nm, at which the saccinimidyl ester reactive dye of the compound represented as formula (1) absorbs the largest amount of light, were obtained by the measurement with ultraviolet-visible near-infrared (UV-VIS-NIR) light. When the quantity of an organic dye added during the reaction was increased, the number of organic dyes conjugated with each dye-conjugated IO20 particle tended to be increased. Furthermore, it was demonstrated that, when the number of organic dyes conjugated with the dye-conjugated IO20 particle was increased, the molar absorption coefficient at 750 nm tended to increase.

The 4 types of dye-conjugated IO20 particles obtained as described above are designated as Composite Particles A, B, C and D in the ascending order from the particle with the least number of organic dyes conjugated with the dye-conjugated IO20 particle. The quantity of an organic dye added during the reaction, the number of dyes conjugated with each composite particle, and the molar absorption coefficient at a wavelength of 750 nm of Composite Particles A, B, C and D are summarized in Table 1.

TABLE 1

| | Quantity of dye added during reaction (double amount) | Number of dyes conjugated with one composite particle (molecules) | Molar absorption coefficient at 750 nm [1/(cm · M)] |
|---|---|---|---|
| A | 20 | 14.4 | 3.46E+06 |
| B | 100 | 33.3 | 7.79E+06 |
| C | 500 | 102.0 | 2.45E+07 |
| D | 1000 | 114.0 | 2.74E+07 |

(Measurement of Photoacoustic Signal Intensity of Composite Particles)

Here, IO20 is referred to as Particle E.

Figure 2:
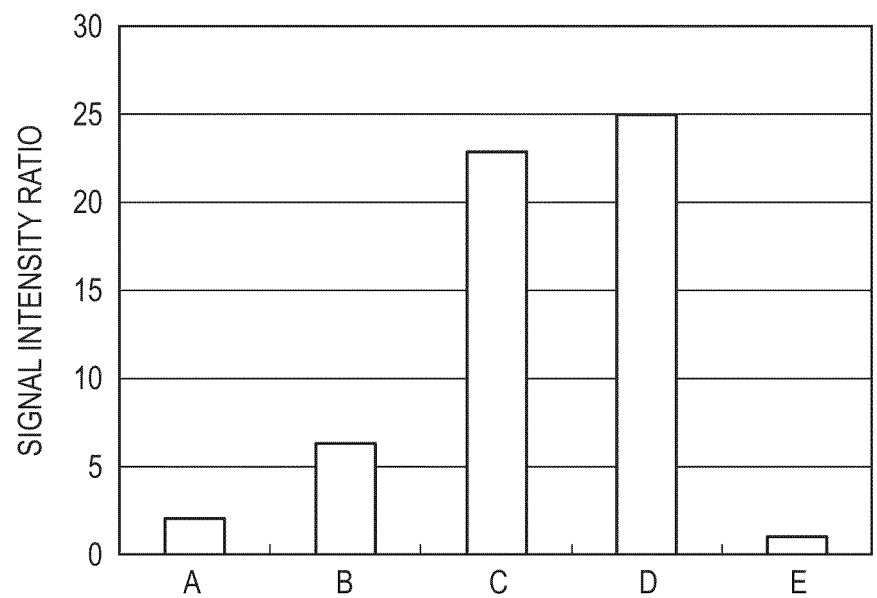
FIG. 2 illustrates the results of measurement of photoacoustic signal intensity of Composite Particles A to D and Particle E.

Measurement of the photoacoustic signal intensity of Composite Particles A, B, C and D, and Particle E was performed. A solution having the same iron concentration as the concentration of Composite Particles A, B, C and D was prepared to measure Particle E. The photoacoustic signal intensity of each composite particle based on the photoacoustic signal intensity of Particle E as 1 is illustrated in FIG. 2.

Composite Particles A, B, C and D conjugated with an organic dye via a single-chain antibody showed more intense signals than the signal of Particle E, which was not conjugated with an organic dye or a single-chain antibody. Furthermore, composite particle conjugated with a larger number of organic dyes showed more intense signals than the signals of composite particles conjugated with a smaller number of organic dyes.

Example 2

(Conjugation of Single-Chain Antibody-IO20 Complex and ICG Dye)

A solution of ICG-Sulfo-OSu (Dojindo Laboratories), an organic dye, in dimethyl sulfoxide was added to the single-chain antibody-IO20 complex prepared in Example 1 in amount of 20, 100, 400 or 1000 times the amount of the complex, and the mixture was slowly stirred at 25° C. for 2 hours. Here, ICG-Sulfo-OSu (Dojindo Laboratories) has a structure of an ICG derivative as shown in the above-mentioned formula (2) and is simply referred to as ICG dye.

After stirring, the mixture was purified using a PD-10 desalting column (GE HEALTHCARE Biosciences) equilibrated with a phosphate buffer (pH=7.4) to obtain 4 types of composite particles conjugated with an ICG dye (hereinafter, ICG dye-conjugated IO20 particles). Here, a lysine (K) residue exists in the sequence of the antibody prepared as described above. Since this lysine residue has a primary amino group which is a nucleophilic group in a side chain, it appears that, when the ICG dye is mixed, a amide bond was formed by a reaction between an amino group and a carboxyl group, and thereby the organic dye and the single-chain antibody were conjugated.

(Measurement of Molar Absorption Coefficient of Composite Particles)

The number of ICG dyes conjugated with the prepared ICG dye-conjugated IO20 particle and the molar absorption coefficient at 780 nm at which the ICG absorbs the largest amount of light, were obtained by the measurement with ultraviolet-visible near-infrared (UV-VIS-NIR) light. When the quantity of an organic dye added during the reaction was increased, the number of ICG dyes conjugated with each ICG dye-conjugated IO20 particle tended to be increased. Furthermore, it was demonstrated that, when the number of ICG dyes conjugated with the ICG dye-conjugated IO20 particle was increased, the molar absorption coefficient at 780 nm tended to increase.

The 4 types of ICG dye-conjugated IO20 particles obtained as described above are designated as Composite Particles F, G, H and I in the ascending order from the particle with the least number of ICG dyes conjugated with the ICG dye-conjugated IO20 particle.

The quantity of an organic dye added during the reaction, the number of dyes conjugated with each composite particle, and the molar absorption coefficient of Composite Particles F, G, H and I at a wavelength of 780 nm are summarized in Table 2.

TABLE 2

| | Quantity of dye added during reaction (double amount) | Number of dyes conjugated with one composite particle (molecules) | Molar absorption coefficient at 780 nm [1/(cm · M)] |
| --- | --- | --- | --- |
| F | 20 | 5.8 | 8.21E+05 |
| G | 100 | 17.0 | 2.24E+06 |
| H | 400 | 49.4 | 6.39E+06 |
| I | 1000 | 63.1 | 8.15E+06 |

(Measurement of Photoacoustic Signal Intensity of Composite Particles)

Here, the single-chain antibody-IO20 complex is designated as Complex J.

Figure 3:
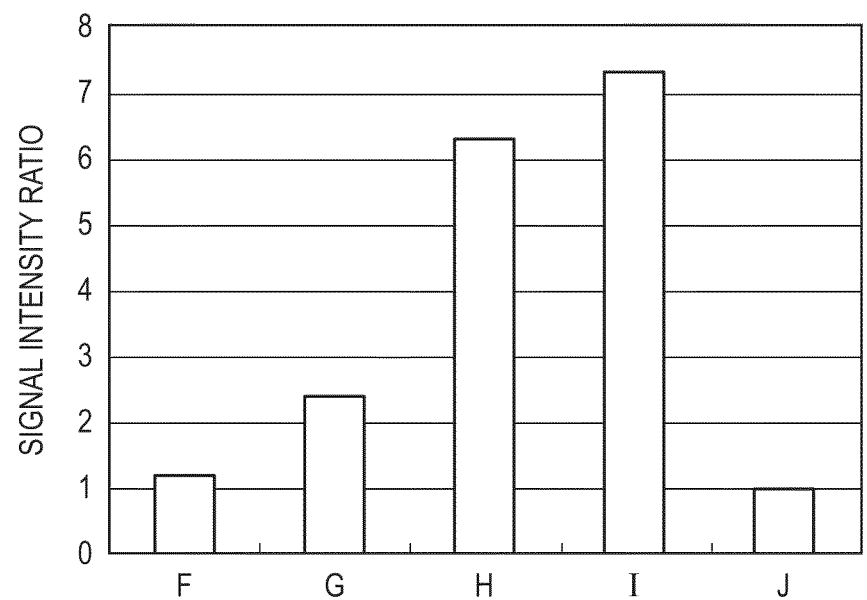
FIG. 3 illustrates the results of measurement of photoacoustic signal intensity of Composite Particles F to I and Complex J.

Measurement of the photoacoustic signal intensity of Composite Particles F, G, H and I and Complex J was performed. The photoacoustic signal intensity of each composite particle based on the photoacoustic signal intensity of Complex J as 1 is summarized in FIG. 3.

Composite Particles F, G, H and I conjugated with an organic dye via a single-chain antibody showed more intense signals than the signal of Complex J, which is not conjugated with an organic dye. Furthermore, composite particles conjugated with larger quantity of an organic dye showed more intense signals than the signals of composite particles conjugated with less quantity of an organic dye.

Example 3

(Synthesis of Polymer Nanoparticle)

4.4 mg of ICG (Pharmaceutical and Medical Device Regulatory Science Society of Japan) was dissolved in 1 mL of methanol (Kishida Chemical Co., Ltd.) to prepare a methanol solution of ICG. The ICG used herein has a structure represented by the above-mentioned formula (3). 9 mg of distearoylphosphatidylcholine (hereinafter, referred to as DSPC; NOF Corporation) was dissolved in 1 mL of chloroform (Kishida Chemical Co., Ltd.) to prepare a chloroform solution of DSPC. 1 mL of the methanol solution of ICG and 1 mL of the chloroform solution of DSPC were mixed, the mixture was stirred for 5 minutes, and the solvent was evaporated at 40° C. under reduced pressure. The ICG-DSPC mixture evaporated to dryness was completely dissolved in 1.6 mL of chloroform to prepare an ICG composition dissolved in chloroform. 20 mg of polylactic acid-glycolic acid copolymer (50:50) (hereinafter, referred to as PLGA; Wako Pure Chemical Industries, Ltd.) having an average molecular weight of 20,000 was dissolved in this composition to prepare a chloroform solution of PLGA.

Subsequently, the chloroform solution of PLGA was added to 20 mL of an aqueous solution of 60 mg of polyoxyethylene sorbitan monolaurate (hereinafter, referred to as Tween20; Tokyo Chemical Industry Co., Ltd.), 7.3 mg of N-(Carbonyl-methoxypolyethyleneglycol 2000)-1,2-distearoyl-sn-glycero-3-phosphoethanolamine sodium salt (hereinafter, referred to as DSPE-020CN; NOF Corporation) which is a polyethylene-glycolated phospholipid having a methoxy group at an end, and 0.7 mg of N-(aminopropylpolyethyleneglycol 2000) carbamyl-distearoylphosphatidyl-ethanolamine (hereinafter, referred to as DSPE-020PA; NOF Corporation) which is a polyethylene-glycolated phospholipid having a primary amino group at an end, and the mixture was stirred at room temperature for 3 minutes. Then, the mixture was treated with an ultrasonic homogenizer for 90 seconds to prepare an O/W emulsion. Subsequently, the emulsion was subjected to rotary evaporation under reduced pressure at 40° C. for 2 hours to remove chloroform from the emulsion solution. Then, the solution was adequately dialyzed against water and passed through a filter (pore size, 0.2 μm; Japan Millipore) to obtain an aqueous solution of a polymer nanoparticle containing an ICG. The obtained particle was designated as ICG-PNP.

The average grain size and the zeta potential of ICG-PNP in water were measured with Zetasizer Nano (Malvern Instruments Ltd.). The average grain size of ICG-PNP was 105 nm (cumulant). The zeta potential was −31 mV.

(Conjugation of ICG-PNP and Single-Chain Antibody)

The single-chain antibody was modified via a primary amino group of ICG-PNP. DSPE-020PA has this primary amino group. First, 0.1 mg (233 nmol) of succinimidyl-[(N-maleimidopropionamido)-diethyleneglycol]ester (hereinafter, referred to as SM(PEG)$_2$; Thermo Fisher Scientific K.K.) was dissolved in 2.9 mL of aqueous ICG-PNP dispersion (ICG-PNP concentration, 4.8×10$^{12}$/mL). Subsequently, 0.33 mL of a borate buffer (pH 8.5) was added. This particle suspension was stirred at room temperature for 2 hours, ICG-PNP into which a maleimide group was introduced (hereinafter, referred to as maleimidated ICG-PNP) and unreacted SM(PEG)$_2$ were separated using a PD-10 desalting column (GE HEALTHCARE Biosciences) and water as a developing solvent to obtain approximately 6 mL of an aqueous solution of maleimidated ICG-PNP. 120 μL of 1 M 2-[4-(2-hydroxyethyl)-1-piperazinyl]ethanesulfonic acid (hereinafter, referred to as HEPES; Wako Pure Chemical Industries, Ltd.)

solution was added to this aqueous solution to obtain an HEPES solution of maleimidated ICG-PNP.

The above-mentioned reduced single-chain antibody was added to the HEPES solution of maleimidated ICG-PNP in an amount of 720 times the amount of maleimidated ICG-PNP, and the mixture was reacted at 4° C. for 15 hours or longer. After reaction, 16.8 nmol of polyethylene glycol (molecular weight 1000, PLS-606; Creative PEG Works) having a thiol group at an end was added to this solution, and the mixture was stirred at room temperature for 30 minutes. Subsequently, this solution was passed through a filter (pore size, 1.2 µm), and then single-chain antibodies that were not conjugated with maleimidated ICG-PNP were removed by ultrafiltration using Amicon Ultra 4 (Japan Millipore) having a pore size of 100 kDa to obtain a complex comprising a single-chain antibody conjugated with ICG-PNP (hereinafter, referred to as single-chain antibody-ICG-PNP complex). Since maleimide group can be strongly bound to thiol group, it appears that, the single-chain antibody and the maleimidated ICG-PNP is bounded to each other via thiol-maleimide coupling.

The quantity of a single-chain antibody conjugated with ICG-PNP was obtained by BCA. The results showed that 491 single-chain antibodies were conjugated with each ICG-PNP. The average grain size and the zeta potential of the single-chain antibody-ICG-PNP complex in water were measured with Zetasizer Nano (Malvern Instruments Ltd.). The results were 109 nm (cumulant) and −40 mV.

(Conjugation of Single-Chain Antibody-ICG-PNP Complex and Organic Dye)

A solution of a saccinimidyl ester reactive dye (Invitrogen), which is a compound represented by the formula (1), in dimethyl sulfoxide was added to the above-mentioned single-chain antibody-ICG-PNP complex in an amount of 3600, 18,000, or 36,000 times the amount of a complex, and the mixture was slowly stirred at 25° C. for 2 hours. After stirring, the mixture was purified using a PD-10 desalting column (GE HEALTHCARE Biosciences) equilibrated with a phosphate buffer (pH=7.4) to obtain 3 types of a single-chain antibody-ICG-PNP complex (hereinafter, referred to as dye-conjugated PNP) conjugated with an organic dye. Here, a lysine (K) residue exists in the sequence of the above-mentioned single-chain antibody prepared in this Example. Since this lysine residue has a primary amino group which is a nucleophilic group in a side chain, it appears that a bond of an amino group and a carboxyl group (amide bond) was formed by mixing the above-mentioned succinimidyl ester reactive dye used in this Example, and thereby the organic dye and the single-chain antibody were conjugated.

(Measurement of Molar Absorption Coefficient of Composite Particles)

The number of dyes conjugated with the prepared dye-conjugated PNP and the molar absorption coefficient at 750 nm, at which the saccinimidyl ester reactive dye of the compound represented as formula (1) absorbs the largest amount of light, were obtained by the measurement with ultraviolet-visible near-infrared (UV-VIS-NIR) light. When the quantity of a dye added during the reaction was increased, the number of organic dyes conjugated with each dye-conjugated PNP tended to be increased. Furthermore, it was demonstrated that, when the number of organic dyes conjugated with the dye-conjugated PNP was increased, the molar absorption coefficient at 750 nm tended to be slightly increase.

Hereinafter, the 3 types of dye-conjugated PNP obtained as described above are designated as Composite Particles K, L and M in the ascending order from the particle with the least number of organic dyes conjugated with the dye-conjugated PNP. The quantity of an organic dye added during the reaction, the number of dyes conjugated with each composite particle, and the molar absorption coefficient at a wavelength of 750 nm of Composite Particles K, L and M are summarized in Table 3.

TABLE 3

| | Quantity of dye added during reaction (double amount) | Number of dyes conjugated with one composite particle (molecules) | Molar absorption coefficient at 750 nm [1/(cm · M)] |
|---|---|---|---|
| K | 3600 | 560 | 6.3E+09 |
| L | 18000 | 860 | 6.3E+09 |
| M | 36000 | 1700 | 6.5E+09 |

(Measurement of Photoacoustic Signal Intensity of Composite Particles)

Here, the single-chain antibody-ICG-PNP complex is designated as Complex N.

Figure 4:
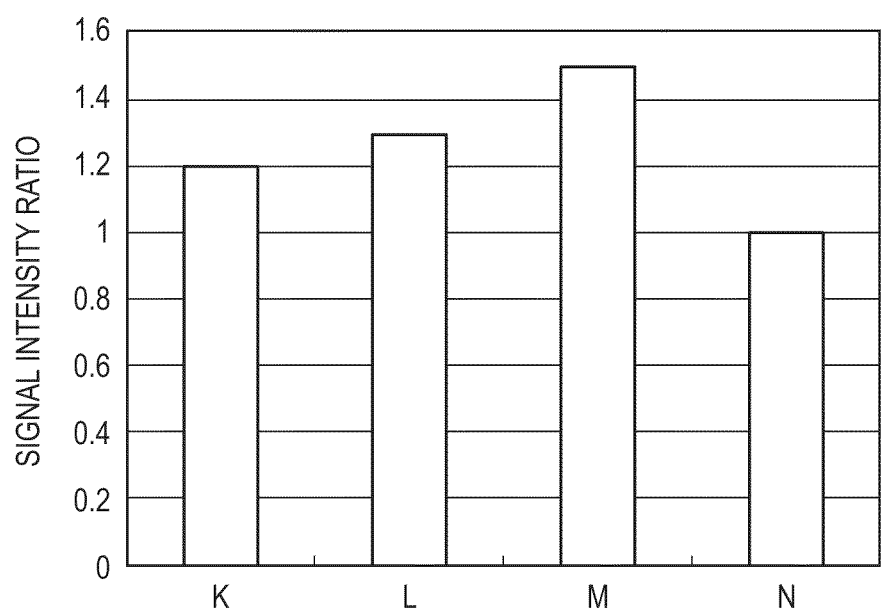
FIG. 4 illustrates the results of measurement of photoacoustic signal intensity of Composite Particles K to M and Complex N.

Measurement of the photoacoustic signal intensity of Composite Particles K, L and M and Complex N was performed. The photoacoustic signal intensity of each Composite Particle based on the photoacoustic signal intensity of Complex N as 1 is summarized in FIG. 4.

Composite Particles K, L and M conjugated with an organic dye via a single-chain antibody showed more intense signals than the signal of Complex N, which is not conjugated with an organic dye. Furthermore, composite particles conjugated with larger quantity of an organic dye showed more intense signals than the signals of composite particles conjugated with less quantity of an organic dye.

Composite Particles K, L and M conjugated with a fluorescent dye via a single-chain antibody showed more intense signals than the signal of Composite Particle N, which is not conjugated with a fluorescent dye. Furthermore, composite particles conjugated with larger quantity of a fluorescent dye showed more intense signals than the signals of composite particles conjugated with less quantity of a fluorescent dye.

Example 4

(Conjugation of Iron Oxide Particle Having Large Grain Size and Single-Chain Antibody)

An iron oxide-containing dextran particle having a maleimide group produced by micromod Partikel-Technolgie (particle size, 50 or 100 nm) (hereinafter, referred to as IO50 or IO100, respectively) was used as an iron oxide particle having a large grain size. The above mentioned reduced single-chain antibody was added in amount of 600 and 2500 times the amounts of IO50 and IO100, respectively. Then the mixture was slowly stirred at 25° C. for 4 hours, and an L-cysteine (Kishida Chemical Co., Ltd.) solution was added to obtain a final concentration of 1 mM. Subsequently, the mixture was purified by size exclusion column chromatography using a column equilibrated with a phosphate buffer (pH=7.4), and then the buffer was replaced with 0.05 M carbonate buffer (pH=9.6) to obtain a single-chain antibody-IO50 complex and a single-chain antibody-IO100 complex. The quantity of a single-chain antibody conjugated with each complex was obtained by quantifying unreacted single-chain antibodies eluted from the above-mentioned size exclusion column. Approximately 110 single-chain antibodies were conjugated to IO50. And, approximately 410 single-chain antibodies were conjugated to IO100. Since maleimide group can be strongly bound to thiol group, it appears that, the single-chain antibody and the IO50 or the IO100 is bounded to each other via thiol-maleimide coupling.

(Conjugation of Single-Chain Antibody-IO50 Complex or Single-Chain Antibody-IO100 Complex and Organic Dye)

A solution of a succinimidyl ester reactive dye (Invitrogen), a compound represented by the above-mentioned formula (1), in dimethyl sulfoxide was added to the above-mentioned single-chain antibody-IO50 complex in an amount of 1100, 2750, or 11,000 times the amount of the complex, and the mixture was slowly stirred at 25° C. for 2 hours. Furthermore, a solution of a succinimidyl ester reactive dye (Invitrogen) in dimethyl sulfoxide was added to the above-mentioned single-chain antibody-IO100 complex in an amount of 4100, 10250, or 41,000 times the amount of the complex, and the mixture was slowly stirred at 25° C. for 2 hours.

After stirring, the mixture was purified using a PD-10 desalting column (GE HEALTHCARE Biosciences) equilibrated with a phosphate buffer (pH=7.4) to obtain composite particles conjugated with an organic dye (hereinafter, referred to as a dye-conjugated IO50 particle and a dye-conjugated IO100 particle). Three types each of the dye-conjugated IO50 particles and the dye-conjugated IO100 particles were obtained.

Here, a lysine (K) residue exists in the sequence of the above-mentioned single-chain antibody prepared in this Example. Since this lysine residue has a primary amino group which is a nucleophilic group in a side chain, it appears that a bond of an amino group and a carboxyl group (amide bond) was formed by mixing the above-mentioned succinimidyl ester reactive dye used in this Example, and thereby the dye and the single-chain antibody were conjugated.

(Measurement of Molar Absorption Coefficient of Composite Particles)

The numbers of organic dyes conjugated with the prepared 3 types of dye-conjugated IO50 particle and 3 types of dye-conjugated IO100 particle and the molar absorption coefficient at 750 nm, at which the saccinimidyl ester reactive dye of the compound represented as formula (1) absorbs the largest amount of light, were obtained by the measurement with ultraviolet-visible near-infrared (UV-VIS-NIR) light. When the quantity of a dye added during the reaction was increased, the number of organic dyes conjugated with each dye-conjugated IO50 particle or dye-conjugated IO100 particle tended to be increased. Furthermore, it was demonstrated that, when the number of organic dyes conjugated with the dye-conjugated IO50 particle or dye-conjugated IO100 particle was increased, the molar absorption coefficient at 750 nm tended to increase.

The 3 types of dye-conjugated IO50 particles obtained as described above are designated as Composite Particles O, P and Q in the ascending order from the particle with the least number of organic dyes conjugated with the dye-conjugated IO50 particle. The 3 types of dye-conjugated IO100 particles obtained as described above are designated as Composite Particles S, T and U in the ascending order from the particle with the least number of organic dyes conjugated with the dye-conjugated IO100 particle. The quantity of an organic dye added during the reaction, the number of dyes conjugated with each composite particle, and the molar absorption coefficient at a wavelength of 750 nm of Composite Particles O, P, Q, S, T and U are summarized in Table 4.

TABLE 4

| | Quantity of dye added during reaction (double amount) | Number of dyes conjugated with one composite particle (molecules) | Molar absorption coefficient at 750 nm [1/(cm · M)] |
|---|---|---|---|
| O | 1100 | 850 | 2.03E+08 |
| P | 2750 | 1600 | 3.90E+08 |
| Q | 11000 | 3400 | 8.20E+08 |
| S | 4100 | 2000 | 4.87E+08 |
| T | 10250 | 3500 | 8.44E+08 |
| U | 41000 | 6100 | 1.49E+09 |

(Measurement of Photoacoustic Signal Intensity of Composite Particles)

Here, the single-chain antibody-IO50 complex is designated as Complex R. The single-chain antibody-IO100 complex is designated as Complex V.

Figure 5A:
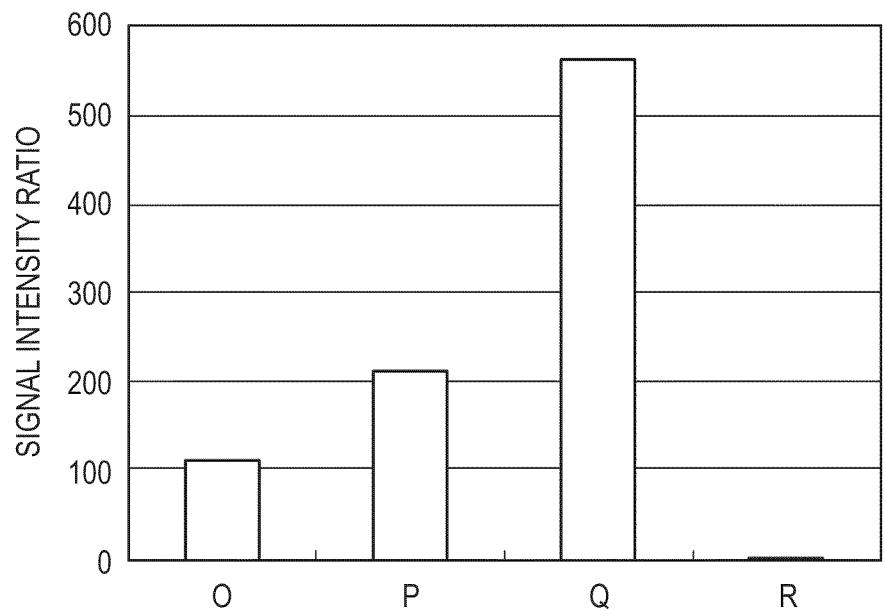
FIG. 5A illustrates the results of measurement of photoacoustic signal intensity of Composite Particles 0 to Q and Complex R.

Measurement of the photoacoustic signal intensity of Composite Particles O, P and Q and complex R was performed. The photoacoustic signal intensity of each composite particle based on the photoacoustic signal intensity of Complex R as 1 is summarized in FIG. 5A. Composite Particles O, P and Q conjugated with an organic dye via a single-chain antibody showed greater intense signals than the signal of Complex R, which was not conjugated with an organic dye. Composite Particles conjugated with larger quantity of organic dyes showed more intense signals than the signals of composite particles conjugated with less quantity of organic dyes.

Figure 5B:
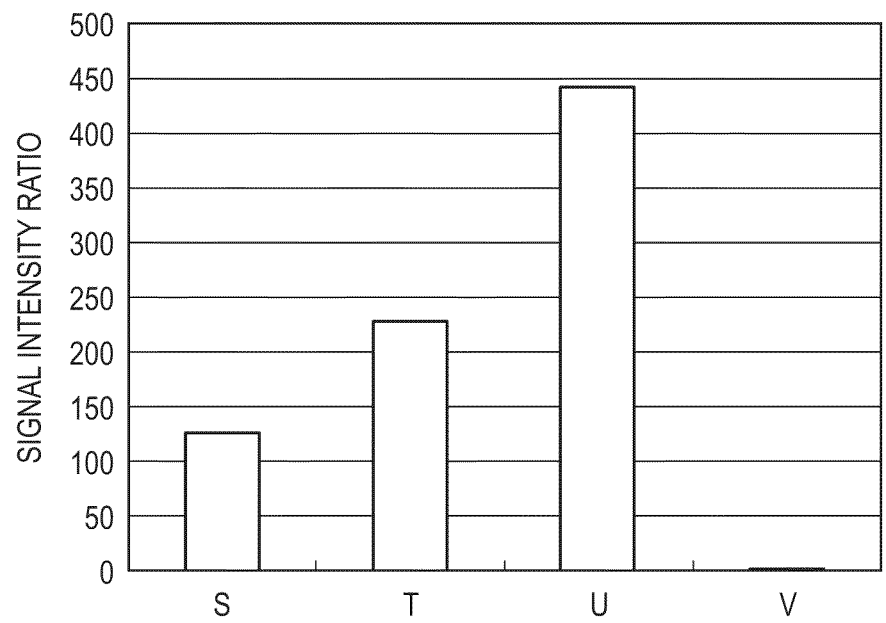
FIG. 5B illustrates the results of measurement of photoacoustic signal intensity of Composite Particle S to U and Complex V.

Measurement of the photoacoustic signal intensity of Composite Particles S, T and U and Complex V was performed. The photoacoustic signal intensity of each composite particle based on the photoacoustic signal intensity of Complex V as 1 is summarized in FIG. 5B. Composite Particles S, T and U conjugated with an organic dye via a single-chain antibody showed greater intense signals than the signal of Complex V, which was not conjugated with an organic dye. Composite particles conjugated with larger quantity of organic dyes showed more intense signals than the signals of composite particles conjugated with less quantity of organic dyes.

(Evaluation of Antibody Function of Dye-Conjugated IO50 Particle and Dye-Conjugated IO100 Particle)

The dye-conjugated IO50 particle and the dye-conjugated IO100 particle, was evaluated for a binding function of an antibody to an antigen (HER2) by surface plasmon resonance (SPR).

SPR was measured with BiacoreX (GE HEALTHCARE Japan). Recombinant Human ErbB2/Fc Chimera (R&D Systems) was dissolved in an acetate buffer (pH 5.0) and immobilized on a first flow cell by amine coupling to a carboxymethyldextran chain of the CM-5 chip surface. The amount of immobilized cells was approximately 1000 Resonance Unit (RU). Meanwhile, after activation, the second flow cell surface was inactivated to be used as a reference when injected. Subsequently, the buffer used for the above-mentioned Composite Particles 0 to V was replaced with a phosphate buffer (pH 7.4) containing 0.005% Tween20. The mixture was adjusted to obtain equal particle concentrations and injected into the two flow cells at a flow rate of 20 μL/min. The duration of measurement consisted of an injection time (binding) of 120 seconds and time elapsed after termination of injection (dissociation) of 120 seconds. After each measurement of a sample, the flow cell surface was washed by injecting an appropriate volume of an aqueous solution of 50 mM sodium hydroxide until the sensorgram returned to baseline.

Figure 6A:
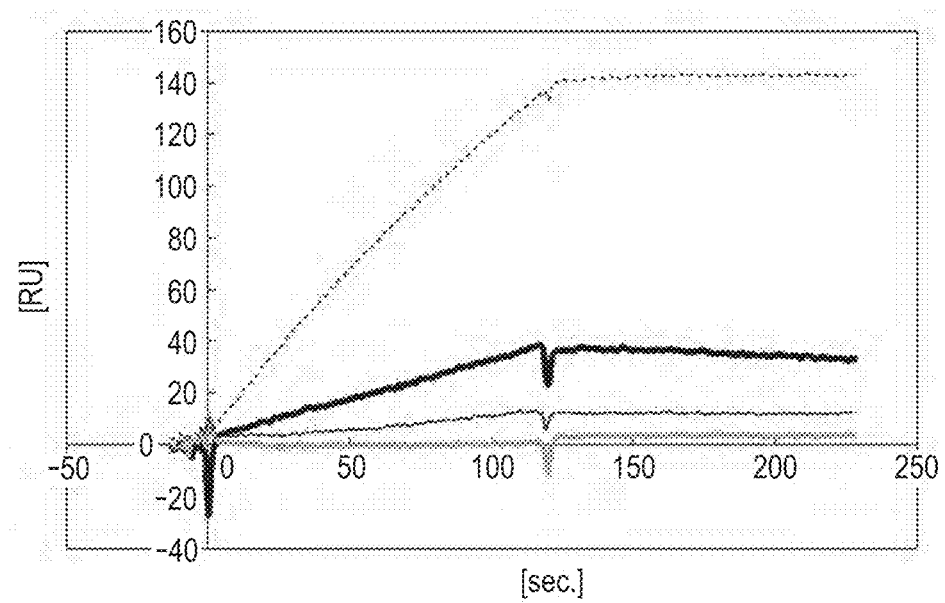
FIG. 6A illustrates the results of evaluation by surface plasmon resonance conducted for antibody binding function of Composite Particles 0 to Q and Complex R.
Figure 6B:
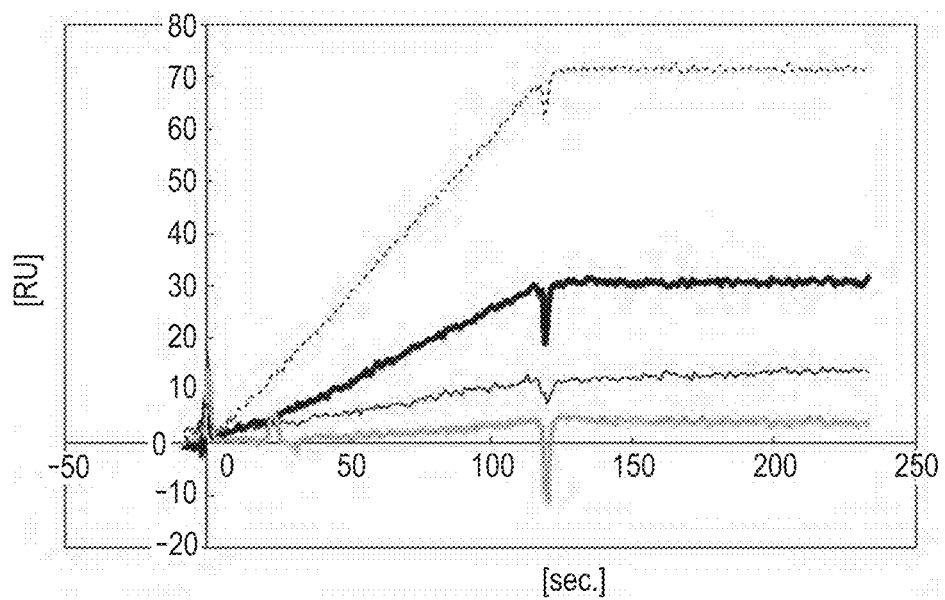
FIG. 6B illustrates the results of evaluation by surface plasmon resonance conducted for antibody binding function of Composite Particle S to U and Complex V.

FIG. 6A illustrates the results of Composite Particles O, P and Q and Complex R. FIG. 6B illustrates the results of Composite Particles S, T and U and Complex V. In FIG. 6A, the black thick line represents Composite Particle O, the black thin line represents Composite Particle P, the dotted thick line represents Composite Particle Q, and the dotted thin line represents Complex R. In FIG. 6B, the black thick line represents Composite Particle S, the black thin line represents Composite Particle T, the dotted thick line represents Composite Particle U, and the dotted thin line represents Complex V. The results indicated that each composite particle conjugated with an organic dye has an ability of a single-chain antibody to bind to an antigen even if an organic dye is conjugated. Composite particles conjugated with a larger quantity of dye showed less increased RU values associated with conjugation with HER2 and decreased binding function as compared with composite particles which are not conjugated with a fluorescent dye.

Subsequently, in the same manner as measurement by the above-mentioned BiacoreX (GE HEALTHCARE Japan), solutions of Composite Particles O and S prepared in several particle concentrations were injected into the two flow cells at a flow rate 20 μL/min, and the dissociation equilibrium constant ($K_D$) was obtained by a kinetic analysis experiment. The duration of measurement consisted of an injection time (binding) of 120 seconds and time elapsed after termination of injection (dissociation) of 120 seconds. After each measurement of a sample, the flow cell surface was washed by injecting an appropriate volume of an aqueous solution of 50 mM sodium hydroxide until the sensorgram returned to baseline. In the binding kinetic analysis experiment, the sensorgram was analyzed using a 1:1 Langmuir fitting model of BIA Evaluation 3.0.2 Software (GE HEALTHCARE). The results demonstrated that the $K_D$ of Composite Particle 0 against HER2 was $8.1 \times 10^{-11}$ [M], and the $K_D$ of Composite Particle S against HER2 was $1.0 \times 10^{-10}$. Both the composite particles were demonstrated to maintain a high binding function to HER2.

Figure 7A:
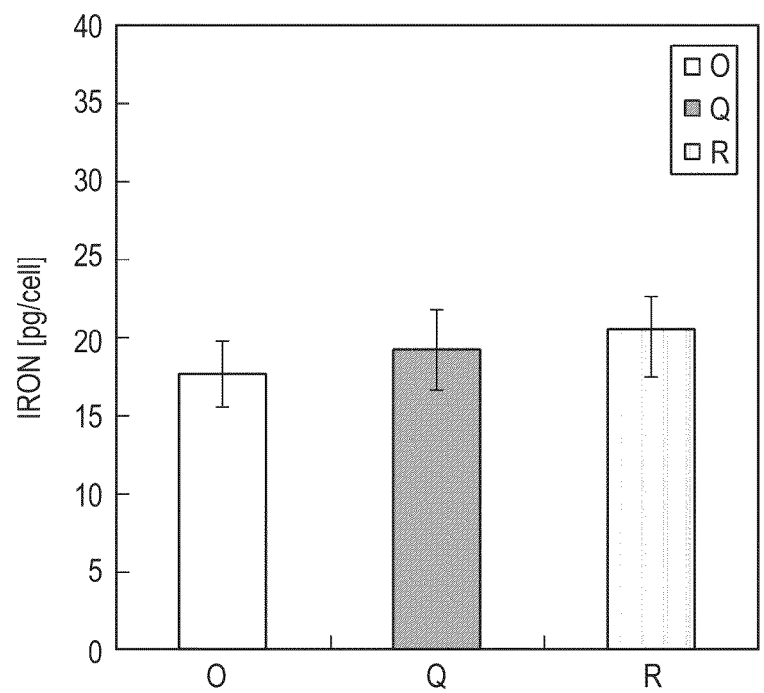
FIG. 7A illustrates the results of evaluation of Composite Particles O and Q and Complex R for antibody binding function to human gastric cancer cell N87 having HER2 on the cell membrane surface.
Figure 7B:
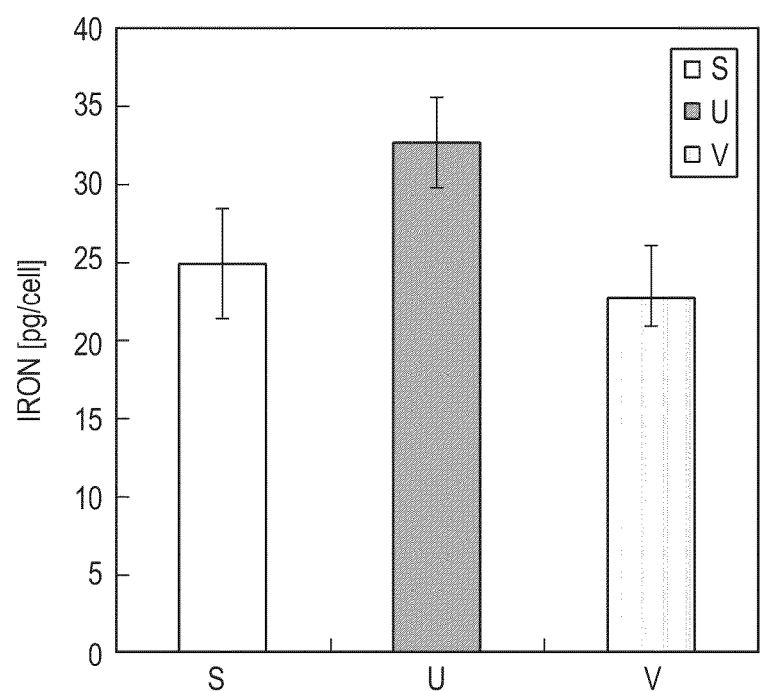
FIG. 7B illustrates the results of evaluation of Composite Particle S and U and Complex V for antibody binding function to human gastric cancer cell N87 having HER2 on the cell membrane surface.

Subsequently, Composite Particles 0 and Q, Complex R, Composite Particles S and U and Complex V were evaluated for the function of binding to human gastric cancer cell N87 (DS Pharma Biomedical Co., Ltd.) having HER2 on the cell membrane surface. On the previous day, the N87 cells were seeded on a 24 well plate ($4 \times 10^5$ cells/well). On the following day, the medium was removed, 200 μL of a growth medium was placed, and Composite Particles 0 and Q, Complexes R and S, Composite Particle U, and Complex V were added. Composite Particles 0 and Q and Complex R were prepared at a particle concentration of 3.2 nM, Composite Particle S and U and Complex V were prepared at a particle concentration of 0.87 nM. Then 100 μL each of these solutions were added. The mixture was allowed to stand at 4° C. for 3 hours, the medium containing these types of composite particles was removed, and the residue was washed twice with 1 mL of PBS. PBS was removed, then 200 μL of 6 M HCl was added to lyse cells, and the plate was incubated at room temperature for 2 hours. 84 μL of pure water, 50 μL of 0.91 mM ascorbic acid, 50 μL of 3.7 M sodium acetate, and 50 μL of aqueous solution of 1.2 mM 4,7-diphenyl-1,10-phenanthrolinedisulfonic acid disodium salt were added to 16 μL each of these cytolysis solutions recovered, and the mixture was incubated at room temperature for 10 minutes. The amount of iron contained in the solution was obtained by measuring the absorbance of this solution at 535 nm. Furthermore, to estimate the volume of endogenous iron in N87, cells were treated without adding composite particles in the same manner as in the above. The amount of iron in a composite particle conjugated with N87 was obtained by subtracting the amount of iron in the solution not containing composite particles from the amount of iron in the solution containing composite particles. The results of Composite Particles 0 and Q and Complex R are shown in FIG. 7A. The results of Composite Particle S and U and Complex V are shown in FIG. 7B. Composite Particles 0 and Q showed strength of binding to N87 similar to the strength of Complex R regardless of the presence or quantity of organic dye binding. Similarly, Composite Particles S and U were demonstrated to have a function of binding to N87 similar to the binding function of Complex V regardless of the presence or quantity of organic dye binding.

(Imaging Using Dye-Conjugated IO100 Particle in a Mouse)

A solution of a succinimidyl ester reactive dye (Invitrogen), a compound represented by the above-mentioned formula (1), in dimethyl sulfoxide was added to the above-mentioned single-chain antibody-IO100 complex in an amount of 410 times the amount of the complex, and the mixture was slowly stirred at 25° C. for 2 hours. After stirring, the mixture was purified using a PD-10 desalting column (GE HEALTHCARE Biosciences) equilibrated with a phosphate buffer (pH=7.4) to obtain a dye-conjugated IO100 particle (hereinafter, referred to as Composite Particle W). Here, a lysine (K) residue exists in the sequence of the above-mentioned single-chain antibody prepared in this Example. Since this lysine residue has a primary amino group which is a nucleophilic group in a side chain, it appears that a bond of an amino group and a carboxyl group (amide bond) was formed by mixing the above-mentioned succinimidyl ester reactive dye used in this Example, and thereby the dye and the single-chain antibody were conjugated.

(Measurement of Molar Absorption Coefficient of Composite Particles)

The number of dyes conjugated with the prepared Composite Particle W and the molar absorption coefficient at 750 nm were obtained by the measurement with ultraviolet-visible near-infrared (UV-VIS-NIR) light. The results showed that 250 organic dyes were conjugated with each Composite Particle W, and that the molar absorption coefficient was $2.3 \times 10^8$ [1/cm/M].

Figure 8:
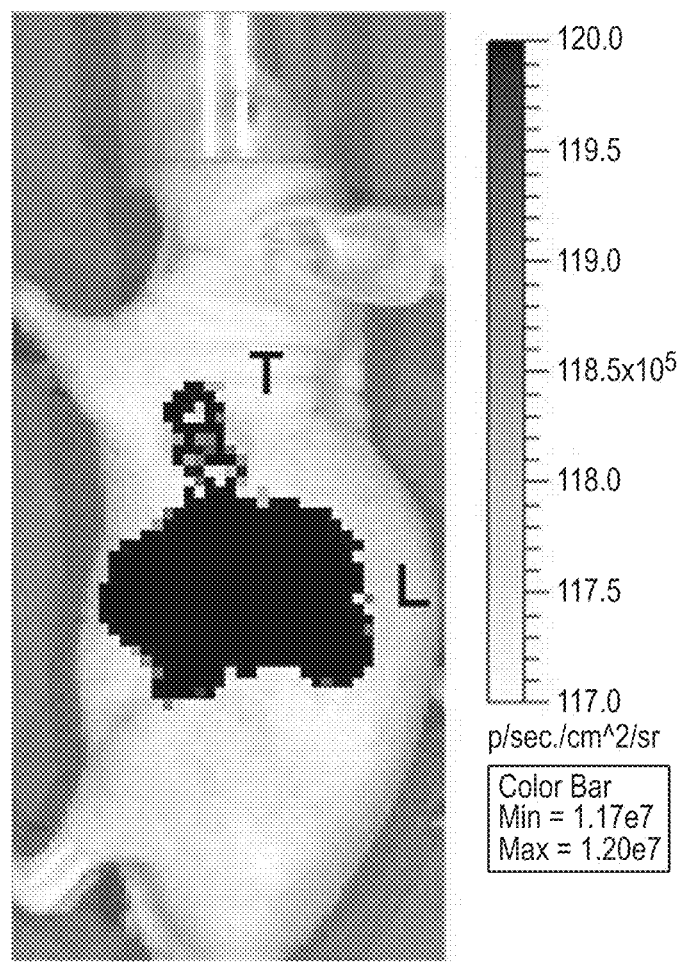
FIG. 8 illustrates the results of fluorescence in vivo tumor imaging of a mouse using Composite Particle W.

Subsequently, the imaging function of the above-mentioned Composite Particle W was evaluated in small animals. As small animals, female outbred BALB/c Slc-nu/nu mice (6 weeks old on purchase) (Japan SLC Inc.) were used. The mice were acclimated using standard feeds and beddings and given food and drinking water ad libitum for 1 week before cancer cells were transplanted. At approximately 2 weeks before an imaging experiment, $2 \times 10^6$ N87 cells and Geltrex (Invitrogen), a tumor forming matrix, were mixed, and the mixture was subcutaneously injected into the left shoulder of the mouse. Tumor cells had been all established by the time of the experiment. The tumor size was approximately 5 mm. The body weights of the mouse were between 17 and 22 g. Composite Particle W dispersed in PBS was administered at a dose of $6.6 \times 10^{-13}$ moles per animal to the above-mentioned mice into which N87 was transplanted, and a systemic fluorescence image was taken 3 days later (FIG. 8). The image was taken with the IVIS200 (Xenogen) system. In FIG. 8, T represents the N87 tumor lesion, and L represents the liver. The image demonstrated that Composite Particle W was accumulated in the tumor lesion. Furthermore, it was also demonstrated that Composite Particle W was accumulated in the liver in addition to the tumor lesion. Furthermore, the muscle and N87 tumor were isolated from the mouse 3 days after administration of Composite Particle W and measured for fluorescence intensity. Comparison of the isolated tissues in fluorescence intensity per weight showed that N87 tumor was twice as large as the muscle, and the Composite Particle W having a function of binding to HER2 was accumulated selectively in N87. It is therefore considered that the composite particles prepared in this Example are suitable as contrast agent for photoacoustic imaging of tumor.

Comparative Example 1

(Conjugation of Iron Oxide Particle Having Carboxyl Group and Single-Chain Antibody)

An iron oxide-containing dextran particle (particle size, 20 nm) having a carboxyl group produced by micromod Partikel-Technolgie (hereinafter, referred to as IOC20) was used as a particle. It should be noted that IOC20 does not have a maleimide group.

An MES buffer (pH=6.3) having a final concentration of 0.1 M that contains 1-ethyl-3-(3-dimethylaminopropyl)carbodiimide hydrochloride (EDAC) having a final concentration of 4 mg/mL and N-hydroxysuccinimide (NHS) having a final concentration of 5 mg/mL was mixed with the IOC20, and the mixture was slowly stirred at 25° C. for 1 hour. Subsequently, the mixture was purified by desalting column chromatography using a column equilibrated with a phosphate buffer (pH=7.4). The above-mentioned single-chain antibody purified by metal chelate affinity chromatography was mixed in an amount of 30 times the amount of the purified IOC20, and the mixture was slowly stirred at 25° C. for 3 hours. Then, an L-glycine solution was added to obtain a final concentration of 1 mM. Subsequently, the mixture was purified by size exclusion column chromatography using a column equilibrated with a phosphate buffer (pH=7.4), and the buffer was replaced with 0.05 M carbonate buffer (pH=9.6) to obtain a complex (hereinafter, referred to as single-chain antibody-IOC20 complex) comprising IOC20 conjugated with a single-chain antibody. The quantity of a single-chain antibody conjugated with each IOC20 particle was obtained by quantifying unreacted single-chain antibodies eluted from the above-mentioned size exclusion column. The result showed that approximately 19 single-chain antibodies were conjugated.

Here, since IOC20 does not have a maleimide group, IOC20 hardly reacts with a thiol group of a single-chain antibody. Therefore, it appears that a single-chain antibody-IOC20 complex is formed by binding a primary amino group which is a nucleophilic group that exists in the side chain of a lysine (K) residue in the sequence of a single-chain antibody, and a carboxyl group of IOC20.

(Conjugation of Single-Chain Antibody-IOC20 Complex and Organic Dye)

A solution of a succinimidyl ester reactive dye (Invitrogen), a compound represented by the above-mentioned formula (1), in dimethyl sulfoxide was added to the above-mentioned single-chain antibody-IOC20 complex in an amount of 300 times the amount of this complex, and the mixture was slowly stirred at 25° C. for 2 hours. After stirring, the mixture was purified using a PD-10 desalting column (GE HEALTHCARE Biosciences) equilibrated with a phosphate buffer (pH=7.4) to obtain a complex comprising a single-chain antibody conjugated with IOC20 (hereinafter, referred to as Composite Particle X).

The number of organic dyes conjugated with the prepared Composite Particle X and the molar absorption coefficient at 750 nm, at which the saccinimidyl ester reactive dye of the compound represented as formula (1) absorbs the largest amount of light, were obtained by the measurement with ultraviolet-visible near-infrared (UV-VIS-NIR) light. The quantity of an organic dye added during the reaction, the number of dyes conjugated with each composite particle, and the molar absorption coefficient at a wavelength of 750 nm of Composite Particles B and X are summarized in Table 5. Although larger quantity of an organic dye was added during the reaction, a smaller number of organic dyes were conjugated with each Composite Particle X during the reaction and the molar absorption coefficient was lower as compared with Composite Particle B. This is because, in Composite Particle X, many of primary amino groups in the side chain of a lysine (K) residue that exists in the of sequence of the single-chain antibody prepared as described above were used for conjugation with IOC-20, only a small number of primary amino groups that can be conjugated with the above-mentioned saccinimidyl ester reactive dyes exists, and therefore a small number of organic dyes were conjugated with each particle.

TABLE 5

| | Quantity of dye added during reaction (double amount) | Number of dyes conjugated with one composite particle (molecules) | Molar absorption coefficient at 750 nm [1/(cm · M)] |
|---|---|---|---|
| B | 100 | 33.3 | 7.79E+06 |
| X | 300 | 6.6 | 1.60E+06 |

(Evaluation of Photoacoustic Characteristics)

Photoacoustic characteristics were evaluated in the same manner as in the above-described method.

Figure 9:
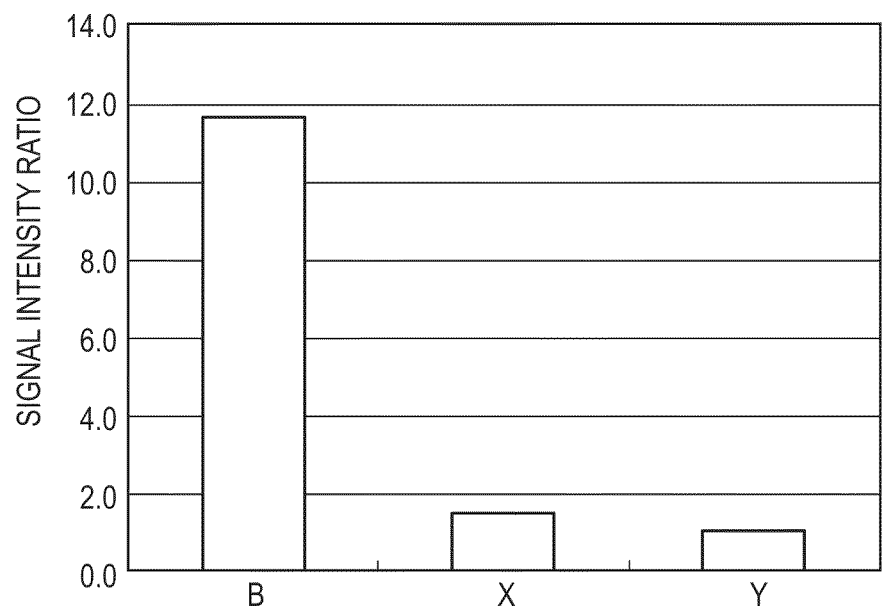
FIG. 9 illustrates the results of measurement of photoacoustic signal intensity of Composite Particles B and X and Complex Y in Comparative Example 1.

Hereinafter, the single-chain antibody-IOC20 complex is referred to as Complex Y. Photoacoustic signal characteristics of Composite Particles B and X were evaluated based on the photoacoustic signal intensity of Complex Y as 1. The ratio of the signal intensity to the photoacoustic signal intensity of Complex Y is illustrated in FIG. 9. Composite Particle B, in which a maleimide group of an iron oxide particle and a thiol group of a single-chain antibody and an amino group of a single-chain antibody and a carboxyl group of an organic dye were bound, showed more intense signals compared with the signal of Complex Y. Meanwhile, Composite Particle X, in which a carboxyl group of an iron oxide particle and an amino group of a single-chain antibody and an amino group of a single-chain antibody and a carboxyl group of an organic dye were bound, showed slightly more intense photoacoustic signals than the signal of Complex Y.

(Evaluation of Antibody Function of Composite Particle X)

Figure 10:
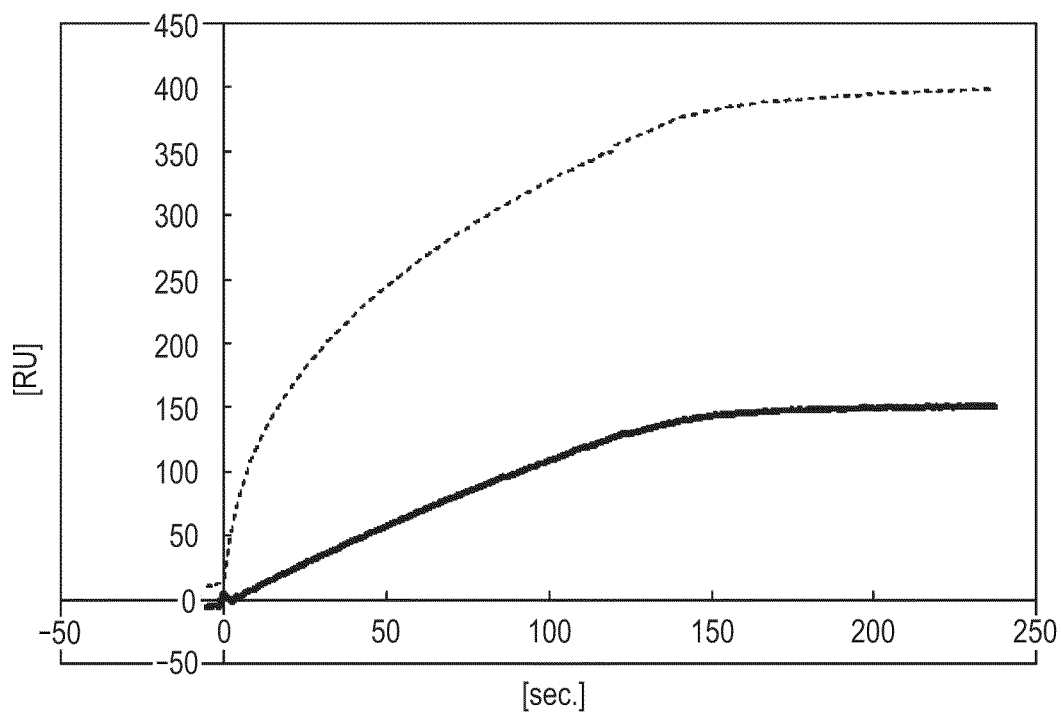
FIG. 10 illustrates the results of evaluation of antibody binding function of Composite Particle X and Complex Y by surface plasmon resonance in Comparative Example 1.

Composite Particle X was evaluated for the function of a single-chain antibody of binding to an antigen (HER2) by surface plasmon resonance (hereinafter, referred to as SPR). SPR was evaluated in the same manner as in the above-described method. After the buffer was replaced with a phosphate buffer (pH 7.4) containing 0.005% Tween20, Composite Particles X and Y were prepared at the same particle concentration, and the solution was injected into both the flow cells at a flow rate 20 μL/min. The measurement time consisted of an injection time (binding) of 120 seconds and time elapsed after termination of injection (dissociation) of 120 seconds. After each measurement of a sample, the flow cell surface was washed by injecting an appropriate volume of an aqueous solution of 50 mM sodium hydroxide until the sensorgram was returned to baseline. FIG. 10 shows the obtained sensorgram. In FIG. 10, the thick line represents Composite Particle X, and the dotted line represents Composite Particle Y. These results indicated that Composite Particle X conjugated with an organic dye has an ability of a single-chain antibody to bind to an antigen although an organic dye was conjugated. Furthermore, Composite Particle X conjugated with an organic dye showed less increased RU values associated with conjugation with HER2 and a decreased binding function as compared with Composite Particle Y, which was not conjugated with an organic dye.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2010-125659, filed Jun. 1, 2010, which is hereby incorporated by reference herein in its entirety.

```
SEQUENCE LISTING
201006010953164030_A163___0083819-
01__12010125659___AAA_3.app
```

```
                              SEQUENCE LISTING

<160> NUMBER OF SEQ ID NOS: 1

<210> SEQ ID NO 1
<211> LENGTH: 257
<212> TYPE: PRT
<213> ORGANISM: Artificial Sequence
<220> FEATURE:
<223> OTHER INFORMATION: single-chain antibody

<400> SEQUENCE: 1

Met Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Asp Val Asn Thr
            20                  25                  30

Ala Val Ala Trp Tyr Gln Gln Lys Pro Gly Lys Ala Pro Lys Leu Leu
        35                  40                  45

Ile Tyr Ser Ala Ser Phe Leu Tyr Ser Gly Val Pro Ser Arg Phe Ser
    50                  55                  60

Gly Ser Arg Ser Gly Thr Asp Phe Thr Leu Thr Ile Ser Ser Leu Gln
65                  70                  75                  80

Pro Glu Asp Phe Ala Thr Tyr Tyr Cys Gln Gln His Tyr Thr Thr Pro
                85                  90                  95

Pro Thr Phe Gly Gln Gly Thr Lys Val Glu Ile Lys Gly Gly Gly Gly
            100                 105                 110

Ser Gly Gly Gly Gly Ser Gly Gly Gly Gly Ser Glu Val Gln Leu Val
        115                 120                 125

Glu Ser Gly Gly Gly Leu Val Gln Pro Gly Gly Ser Leu Arg Leu Ser
    130                 135                 140

Cys Ala Ala Ser Gly Phe Asn Ile Lys Asp Thr Tyr Ile His Trp Val
145                 150                 155                 160

Arg Gln Ala Pro Gly Lys Gly Leu Glu Trp Val Ala Arg Ile Tyr Pro
                165                 170                 175

Thr Asn Gly Tyr Thr Arg Tyr Ala Asp Ser Val Lys Gly Arg Phe Thr
            180                 185                 190

Ile Ser Ala Asp Thr Ser Lys Asn Thr Ala Tyr Leu Gln Met Asn Ser
        195                 200                 205

Leu Arg Ala Glu Asp Thr Ala Val Tyr Tyr Cys Ser Arg Trp Gly Gly
    210                 215                 220

Asp Gly Phe Tyr Ala Met Asp Tyr Trp Gly Gln Gly Thr Leu Val Thr
225                 230                 235                 240

Val Ser Ser Ala Ala Ala Leu Glu His His His His His His Gly Gly
                245                 250                 255

Cys
```

What is claimed is:

1. A composite particle having
   a particle,
   a single-chain antibody which includes an antigen recognition region and a region other than the antigen recognition region and which is conjugated with the particle, and
   an organic dye conjugated with the single-chain antibody,
   wherein the region other than the antigen recognition region of the single-chain antibody has a thiol group, and a functional group of the particle is bound to the thiol group.

2. The composite particle according to claim 1, wherein the single-chain antibody has at least any one of an amino group, carboxyl group and hydroxyl group, and a functional group of the organic dye is bound to the at least any one of the amino group, carboxyl group and hydroxyl group.

3. The composite particle according to claim 1, wherein the particle has at least any one of an iron oxide particle and indocyanine green.

4. The composite particle according to claim 1, wherein the single-chain antibody has an amino acid sequence of SEQ ID NO: 1:

```
                                         (SEQ ID NO: 1)
MDIQMTQSPSSLSASVGDRVTITCRASQDVNTAVAWYQQKPGKA

PKLLIYSASFLYSGVPSRFSGSRSGTDFTLTISSLQPEDFATYYCQQHYT

TPPTFGQGTKVEIKGGGGSGGGGSGGGGSEVQLVESGGGLVQPGGSLRLS

-continued
CAASGFNIKDTYIHWVRQAPGKGLEWVARIYPTNGYTRYADSVKGRFTIS

ADTSKNTAYLQMNSLRAEDTAVYYCSRWGGDGFYAMDYWGQGTLVTVSSA

AALEHHHHHHGGC.
```

5. A contrast agent for photoacoustic imaging containing the composite particle according to claim 1 and a dispersion medium.

6. A composite particle having
   a particle,
   a single-chain antibody which includes an antigen recognition region and a region other than the antigen recognition region and which is conjugated with the particle, and
   an organic dye conjugated with the single-chain antibody,
   wherein the single-chain antibody and the particle are conjugated via a thiol group in the region other than the antigen recognition region of the single-chain antibody.

7. The composite particle according to claim 6, wherein the single-chain antibody and the organic dye are conjugated via at least any one of amino, hydroxyl and carboxyl groups in the single-chain antibody.

8. A method for producing a composite particle, comprising binding a functional group contained in a particle to a thiol group contained in a region other than an antigen recognition region in a single-chain antibody that includes the antigen recognition region and the region other than the antigen recognition region and binding a functional group of an organic dye to at least any one of amino, carboxyl and hydroxyl groups of the single-chain antibody.

* * * * *